(12) United States Patent
Takai

(10) Patent No.: US 7,786,224 B2
(45) Date of Patent: Aug. 31, 2010

(54) LIQUID COMPOSITION OF ALICYCLIC DIEPOXIDE, CURING AGENT AND/OR CURING ACCELERATOR

(75) Inventor: Hideyuki Takai, Ohtake (JP)

(73) Assignee: Daicel Chemical Industries, Ltd, Osaka (JP)

( * ) Notice: Subject to any disclaimer, the term of this patent is extended or adjusted under 35 U.S.C. 154(b) by 467 days.

(21) Appl. No.: 10/883,162

(22) Filed: Jul. 1, 2004

(65) Prior Publication Data

US 2004/0242839 A1    Dec. 2, 2004

Related U.S. Application Data

(62) Division of application No. 10/103,645, filed on Mar. 20, 2002, now abandoned.

(30) Foreign Application Priority Data

| Mar. 23, 2001 | (JP) | ............................. 2001-84195 |
| May 14, 2001 | (JP) | ............................ 2001-143835 |
| Jun. 26, 2001 | (JP) | ............................ 2001-193430 |

(51) Int. Cl.
*C08G 59/48* (2006.01)
*C08L 63/00* (2006.01)
*C07D 301/14* (2006.01)

(52) U.S. Cl. .................. 525/524; 549/525; 525/525; 525/526; 525/533

(58) Field of Classification Search ............... None
See application file for complete search history.

(56) References Cited

U.S. PATENT DOCUMENTS

| 3,075,955 | A |   | 1/1963 | Starcher et al. |
| 3,271,371 | A |   | 9/1966 | Tinsley et al. |
| 3,278,456 | A | * | 10/1966 | Starcher et al. ........... 528/365 |
| 5,294,582 | A | * | 3/1994 | Miyazono et al. ........... 502/164 |
| 5,378,736 | A | * | 1/1995 | Fujiwa et al. ................ 522/170 |
| 5,494,977 | A | * | 2/1996 | Harano et al. ................ 525/438 |
| 5,985,510 | A | * | 11/1999 | Akutsu et al. ................ 430/269 |
| 6,210,790 | B1 | * | 4/2001 | Crivello ....................... 428/325 |
| 6,268,403 | B1 | * | 7/2001 | Crivello ........................ 522/31 |
| 6,322,892 | B1 | * | 11/2001 | Takami ....................... 428/418 |
| 6,348,523 | B1 | * | 2/2002 | Tachikawa et al. .......... 523/462 |
| 6,566,029 | B2 | * | 5/2003 | Kawamura et al. .......... 430/138 |
| 6,779,656 | B2 | * | 8/2004 | Klettke et al. ................ 206/219 |
| 7,345,140 | B2 | * | 3/2008 | Miyake et al. .............. 528/406 |
| 2003/0059618 | A1 | * | 3/2003 | Takai ........................ 428/413 |
| 2004/0242839 | A1 | * | 12/2004 | Takai ........................ 528/408 |

FOREIGN PATENT DOCUMENTS

| DE | 1099733 | | * | 2/1961 |
| DE | 1418465 | A1 | * | 10/1968 |
| DE | 3211305 | | * | 9/1983 |
| EP | 0090239 | | | 10/1983 |
| EP | 0844262 | | | 5/1998 |
| EP | 0950677 | | | 10/1999 |
| GB | 758728 | A | * | 10/1956 |
| GB | 996064 | | * | 6/1965 |
| GB | 2008593 | A | * | 6/1979 |
| JP | 48-29899 | A | * | 4/1973 |
| JP | 50-32500 | A | * | 3/1975 |
| JP | 53-35999 | A | * | 4/1978 |
| JP | 54-3006 | A | * | 1/1979 |
| JP | 59-136321 | A | * | 8/1984 |
| JP | 61-213204 | A | * | 9/1986 |
| JP | 2-169620 | A | * | 6/1990 |
| JP | 5-194716 | A | * | 8/1993 |
| JP | 5-239043 | A | * | 9/1993 |
| JP | 5-279451 | A | * | 10/1993 |
| JP | 7-45126 | A | * | 2/1995 |
| JP | 7-196774 | A | * | 8/1995 |
| JP | 9-124767 | A | * | 5/1997 |
| JP | 9-176288 | A | * | 7/1997 |
| JP | 11-1631 | A | * | 1/1999 |
| JP | 11-106474 | A | * | 4/1999 |
| JP | 11-255863 | A | * | 9/1999 |
| JP | 2003-13001 | A | * | 1/2003 |
| JP | 2003-73457 | A | * | 3/2003 |
| JP | 2003-109780 | A | * | 4/2003 |
| JP | 2003-519705 | A | * | 6/2003 |
| JP | 2004-99467 | A | * | 4/2004 |
| JP | 2004-182648 | A | * | 7/2004 |
| JP | 2004-204228 | A | * | 7/2004 |
| JP | 2004-262874 | A | * | 9/2004 |
| WO | 00/03300 | | | 1/2000 |
| WO | WO 02/076966 | A1 | * | 10/2002 |

OTHER PUBLICATIONS

HCAPLUS accession No. 1972:526335 for the Neftekhimiya article by Yur've et al., vol. 12, No. 3, 1972, four pages.*
Yu've et al., "Oxidation of dienes by hydroperoxides," Neftehimiya, vol. 12, No. 3, 1972, pp. 353-357.*

* cited by examiner

*Primary Examiner*—Robert Sellers
(74) *Attorney, Agent, or Firm*—Locke Lord Bissell & Liddell, LLP

(57) ABSTRACT

A liquid epoxy resin composition of an epoxy resin, a curing agent, and a curing accelerator, where the epoxy resin is an alicyclic epoxy compound present in an amount from 100 to 30% by weight. The alicyclic epoxy compound is preferably produced by using a percarboxylic acid having a water content of 2% by weight. The curing agent is preferably a liquid acid anhydride.

11 Claims, No Drawings

LIQUID COMPOSITION OF ALICYCLIC DIEPOXIDE, CURING AGENT AND/OR CURING ACCELERATOR

This application is a division of U.S. Ser. No. 10/103,645 filed Mar. 20, 2002, now abandoned, the entirety of which is incorporated herein by reference as if fully set forth herein.

FIELD OF THE INVENTION

Invention I relates to a method of producing an epoxy resin compound. More particularly, it relates to a method of producing an alicyclic epoxy compound having a specific structure by oxidizing an alicyclic olefin compound with an aliphatic percarboxylic acid having low water content. The alicyclic epoxy compound is useful for use in coatings, inks, adhesives, sealants, encapsulants, stabilizers or the like.

Invention II relates to an epoxy resin composition containing an alicyclic epoxy compound as a main component and applications thereof. More particularly, it relates to an epoxy resin composition which can be cured by heating, thereby obtaining a cured product having good moisture and heat resistance and transparency, and applications thereof for photosemiconductor encapsulation.

Invention III relates to an ultraviolet rays-curable can-coating composition containing an alicyclic epoxy compound as a main component, which can be cured by ultraviolet irradiation, thereby forming a coating film having excellent film performances such as processability, adhesion, hardness and scratch resistance, particularly excellent outer appearance and retort resistance of films, and to a process of producing a coated metal can using this composition.

BACKGROUND OF THE INVENTION

Background Art Regarding the Inventions I and II

At present, various kinds of diepoxy compounds having two alicyclic skeletons in the molecule are commercially available. For example, there are Celloxide 2021 (3,4-epoxy-cyclohexylmethyl-3',4'-epoxycyclohexane carboxylate), Celloxide 3000 (1,2,8,9-diepoxy limonene), and Celloxide 2081 ($\in$-caprolactone monomer or oligomer each having 3,4-epoxycyclohexyl methanol and 3,4-epoxycyclohexane carboxylic acid ester bonded to both terminals thereof, respectively), all being products from Daicel Chemical Industries, Ltd.

Celloxide 3000 has methyl group-on carbon constituting epoxy group, so that reactivity of epoxy group is low as compared with a compound having no methyl group. For this reason, an alicyclic epoxy resin has mainly been used in the case of, for example, preferentially achieving low viscosity or high Tg.

Further, Celloxide 2021 and Celloxide 2081 each has an ester group in the molecule thereof, and therefor has hydrolyzability. Those also have poor moisture and heat resistance as compared with bisphenol type epoxy compounds.

For the above reasons, in the case where those compounds are used under high temperature and high humidity, or under conditions that would generate a strong acid, decrease in physical properties of the resulting cured product has often occurred.

As proposals to overcome those problems, JP-09255764 A describes an epoxy resin for photosemiconductor encapsulation, containing a diglycidyl ether of a hydrogenated bisphenol A. This epoxy resin, however, has the problems on discoloration, weatherability, heat resistance and the like of a cured product. JP-10156952 A describes a resin composition for optical three-dimensional shapes using the same alicyclic epoxy compound as in the present invention, but it does not contain any description regarding utilization of the resin composition for encapsulation of photosemiconductor. Further, JP-2000063485A describes a build-up curable composition using a composition comprising a specific alicyclic epoxy compound and a multivalent epoxy compound having a polyhydric phenol skeleton, but its main feature does not reside in heat resistance and transparency.

On the other hand, JP-48029899 A describes that a compound wherein X in an alicyclic epoxy compound (A) represented by the formula (I) described later is —$CH_2$— is synthesized, and curing reaction with an acid anhydride is conducted using this compound, to thereby improve physical properties of the resulting cured product as compared with conventional alicyclic epoxy compounds. However, synthesis of the epoxy compound uses perbenzoic acid, and therefore this makes it difficult to utilize the synthesis industrially.

In JP-58172387 A, a percarboxylic acid is synthesized from hydrogen peroxide, an acidic catalyst and an organic acid, the resulting percarboxylic acid is extracted with an organic solvent, and epoxidation is conducted using the extracted percarboxylic acid. This involves the problems that the operation requires many steps and moreover the amount of wastes is large, whereby the entire process becomes complicated. Further, considering extraction efficiency and costs for extracting the percarboxylic acid, the solvent to be used will be for example, benzene, but use of such the solvent is not preferable from the viewpoint of toxicity. In view of the above circumstances, it has been demanded to develop an epoxy resin having an alicyclic skeleton which does not have an ester group in the molecule thereof, and its efficient production method.

Accordingly, an object of the invention I is to provide a method of conducting epoxidation of an alicyclic olefin compound efficiently and economically, and also by using a solvent having low toxicity.

An object of the invention II is to provide an epoxy resin composition for photosemiconductor encapsulation, which provides a cured product having excellent moisture and heat resistance and transparency.

Background Art Regarding the Invention III

Conventionally, examples of ultraviolet rays-curable coating compositions include: cationic polymerization type coating materials containing a cation-polymerizable compound having an epoxy group or a vinyl group and a cationic polymerization initiator that generates a cation by ultraviolet irradiation; and radical polymerization type coating materials containing a radical polymerizable compound having a radically polymerizable unsaturated group and a radical polymerization initiator that generates radical by ultraviolet irradiation.

The radical polymerization type coating material has a characteristic that curing rate is relatively fast. However, it has problems that adhesion to a raw material and processability are insufficient, surface curability is poor due to inhibition of curing by oxygen, and in particular, in the case of using the coating material in the form of a thin film (2 to 8 µm), facilities for nitrogen sealing or the like are necessary.

On the other hand, the cationic polymerization type coating material has the advantages that adhesion to a raw material and processability are good as compared with the radical polymerization type coating material, and that facilities for nitrogen sealing or the like are not necessary. However, it has problems that because curing rate is slow, film performances, in particular film appearance and retort resistance, are insufficient.

Further, both of the radical polymerization type coating material and cationic polymerization type coating material have the problem that curability is insufficient in low irradiation dose (less than 100 mj/cm²).

The reason for this is considered to be that, for example, although many of alicyclic epoxy compounds suitable for cationic curing have an ester linkage in the molecule, the ester linkage reacts with cation species, thereby inhibiting polymerization of epoxy.

For example, JP-10158581 A describes an ultraviolet rays-curable can-coating composition containing a compound having an alicyclic epoxy group in the molecule, a compound having an oxetane ring in the molecule, a specific copolymer and a cationic polymerization initiator. However, this coating composition has problems on hardness in hot water pertaining to retort resistance, film appearance, impact resistance, and the like, due to the above reasons.

Therefore, an object of the invention III is to provide an ultraviolet rays-curable can-coating composition and a process for producing a coated metal can.

DISCLOSURE OF THE INVENTION

As a result of extensive research to achieve the object of the invention I, the present inventors have found that the problem of the invention I can be overcome by epoxidizing a compound having two alicyclic olefin skeletons, with an aliphatic percarboxylic acid having low water content. The invention I has been completed based on this finding.

As a result of extensive research to achieve the object of the invention II, the present inventors have found that if an alicyclic epoxy compound having a structure such that an ester linkage is not present therein and methyl group is not present on carbon constituting an alicyclic epoxy is used, an epoxy resin composition for photosemiconductor encapsulation, which provides a cured product having excellent moisture and heat resistance and transparency, can be obtained to thereby overcome the problem of the invention II. The invention II has been completed based on this finding.

As a result of extensive research to achieve the object of the invention III, the present inventors have found that when an alicyclic epoxy compound having a specific structure is used in a given amount, a coating film can be formed, which is a thin coating film that does not require facilities for, for example, nitrogen sealing, can be cured by ultraviolet irradiation in small irradiation dose, and is excellent in film performances required as a can coating material, such as processability, adhesive properties, hardness and scratch resistance, particularly film appearance and retort resistance, and also a coating film exhibiting excellent hardness in hot water can be formed by performing heating after ultraviolet irradiation. The invention III has been completed based on these findings.

SUMMARY OF THE INVENTION

That is, a first aspect of the present invention relates to a method of producing an alicyclic epoxy compound (A) represented by the following formula (I):

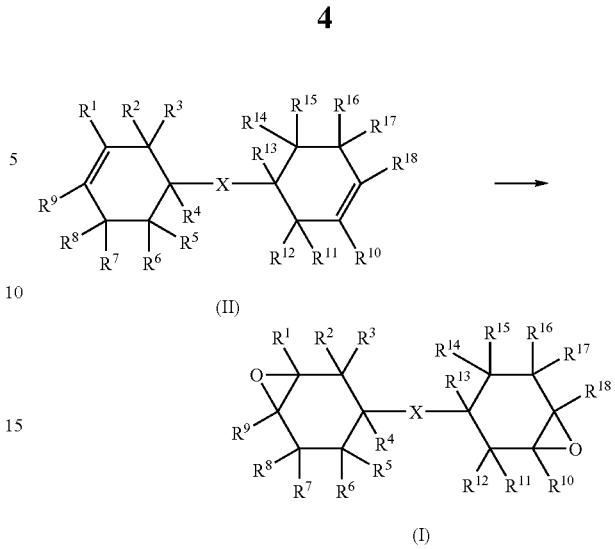

(wherein X represents a divalent group selected from oxygen atom, sulfur atom, —SO—, —SO$_2$—, —CH$_2$—, —C(CH$_3$)$_2$—, —CBr$_2$—, —C(CBr$_3$)$_2$—, —C(CF$_3$)$_2$—, —C(CCl$_3$)$_2$— and —CH(C$_6$H$_5$)—, or a single bond linking two alicyclic rings; and R$^1$ to R$^{18}$ are the same or different and each represents hydrogen atom, halogen atom, a hydrocarbon group which may contain oxygen atom or halogen atom, or an alkoxyl group which may have substituent groups), the method characterized by comprising epoxidizing an alicyclic olefin compound represented by the above formula (II) using an aliphatic percarboxylic acid having water content of 2% by weight or less.

A second aspect of the present invention relates to a method of producing an alicyclic epoxy compound (A) according to the first aspect, characterized in that the aliphatic percarboxylic acid is obtained by oxidation of the corresponding aldehyde with oxygen.

A third aspect of the present invention relates to a method of producing an alicyclic epoxy compound (A) according to the first or second aspect, characterized in that the water content in the aliphatic percarboxylic acid is 0.8% by weight or less.

A fourth aspect of the present invention relates to a method of producing an alicyclic epoxy compound (A) according to any one of the first to third aspects, characterized in that the aliphatic percarboxylic acid is peracetic acid.

A fifth aspect of the present invention relates to a liquid epoxy resin composition comprising an epoxy resin, and a curing agent and/or a curing accelerator, characterized in that the epoxy resin comprises in an amount of 100 to 20% by weight an alicyclic epoxy compound (A) represented by the following formula (I):

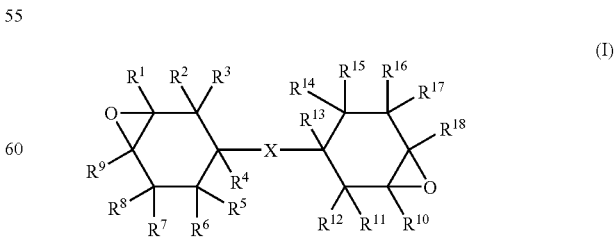

(wherein X represents a divalent group selected from oxygen atom, sulfur atom, —SO—, —SO$_2$—, —CH$_2$—, —C $-(CH_3)_2-$, $-CBr_2-$, $-C(CBr_3)_2-$, $-C(CF_3)_2-$, $-C(CCl_3)_2-$ and $-CH(C_6H_5)-$, or a single bond linking two alicyclic rings; and $R^1$ to $R^{18}$ are the same or different and each represents hydrogen atom, halogen atom, a hydrocarbon group which may contain oxygen atom or halogen atom, or an alkoxyl group which may have substituent groups).

A sixth aspect of the present invention relates to a liquid epoxy resin composition according to the fifth aspect, characterized in that the alicyclic epoxy compound (A) represented by the formula (I) is an epoxy compound produced by using percarboxylic acid having water content of 1% by weight or less.

A seventh aspect of the present invention relates to a liquid epoxy resin composition according to the fifth or sixth aspect, characterized in that the curing agent is an initiator which releases a substance initiating cationic polymerization by heating.

An eighth aspect of the present invention relates to a liquid epoxy resin composition according to any one of the fifth to seventh aspects, characterized in that the curing agent is a liquid acid anhydride.

A ninth aspect of the present invention relates to a liquid epoxy resin composition which is obtained by adding 110 to 160 parts by weight of a curing agent (C) which is a liquid acid anhydride and 3 to 7 parts by weight of a curing accelerator, to 100 parts by weight of the alicyclic epoxy compound (A) represented by the formula (I) of the fifth aspect, or by further adding 0.1 to 20 parts by weight of an initiator (E) that releases cation species upon heating, to 100 parts by weight of the alicyclic epoxy compound (A).

A tenth aspect of the present invention relates to a liquid epoxy resin composition according to any one of the fifth to ninth aspects, which is used for photosemiconductor encapsulation.

An eleventh aspect of the present invention relates to a photosemiconductor device, comprising a photosemiconductor element encapsulated with the epoxy resin composition for photosemiconductor encapsulation according to the tenth aspect. A twelfth aspect of the present invention relates to an ultraviolet rays-curable can-coating composition comprising: 10 to 100 parts by weight of an alicyclic epoxy compound (A) represented by the following formula (I):

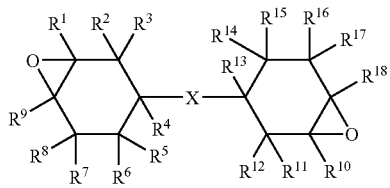

(I)

(wherein X represents a divalent group selected from oxygen atom, sulfur atom, $-SO-$, $-SO_2-$, $-CH_2-$, $-C(CH_3)_2-$, $-CBr_2-$, $-C(CBr_3)_2-$, $-C(CF_3)_2-$, $-C(CCl_3)_2-$ and $-CH(C_6H_5)-$, or a single bond linking two alicyclic rings; and $R^1$ to $R^{18}$ are the same or different and each represents hydrogen atom, halogen atom, a hydrocarbon group which may contain oxygen atom or halogen atom, and an alkoxyl group which may have substituent groups); 0 to 90 parts by weight of a compound having an alicyclic epoxy group in the molecule and also having an ester linkage and/or an epoxy compound (B) having a glycidyl group; 1 to 50 parts by weight of a copolymer (F) having at least one glycidyl group and/or alicyclic epoxy group in the molecule, per 100 parts by weight of the sum of the compound (A) and the compound (B); and 0.01 to 20 parts by weight of a cationic polymerization initiator (G) which generates a cation by ultraviolet irradiation.

A thirteenth aspect of the present invention relates to an ultraviolet rays-curable can-coating composition according to the twelfth aspect, characterized in that the copolymer (F) is a copolymer of glycidyl group-containing polymerizable unsaturated monomer and/or alicyclic epoxy group-containing polymerizable unsaturated monomer, and other polymerizable monomer.

A fourteenth aspect of the present invention relates to an ultraviolet-curing can coating composition according to any one of the twelfth to thirteenth aspects, which further contains a lubricity-imparting agent in an amount of 0.01 to 10 parts by weight based on 100 parts by weight of the total amount of the alicyclic epoxy compound (A) and the epoxy compound (B) represented by the above formula (I).

A fifteenth aspect of the present invention relates to an ultraviolet rays-curable can-coating composition according to any one of the twelfth to fourteenth aspects, which further contains fine particles of resins in an amount of 0.1 to 50 parts by weight per 100 parts by weight of the total amount of the alicyclic epoxy compound (A) represented by the above formula (I) and the epoxy compound (B). A sixteenth aspect of the present invention relates to an ultraviolet rays-curable can-coating composition according to any one of the twelfth to fifteenth aspects, characterized in that the alicyclic epoxy compound (A) represented by the formula (I) is an epoxy compound produced by using an aliphatic percarboxylic acid having water content of 2% by weight or less.

A seventeenth aspect of the present invention relates to a process of producing a coated metal can, which comprises applying the ultraviolet rays-curable can-coating composition according to any one of the twelfth to sixteenth aspects to a metal plate, a resin film-laminated metal plate or a metal can molded from those metal plates, and irradiating the coated product with ultraviolet rays to cure the resulting coating film.

DETAILED DESCRIPTION OF THE INVENTION

Best Mode for Carrying Out the Invention

First, the invention I is described in detail below.

The alicyclic epoxy compound (A) represented by the above-mentioned formula (I) in the invention I is produced by oxidizing an alicyclic olefin compound represented by the formula (II) with an aliphatic percarboxylic acid having a water content of 2% by weight or less.

The alicyclic olefin compound used as a raw material is generally synthesized by dehydration reaction of a compound having the corresponding hydroxyl group.

The alicyclic olefin compound represented by the formula (II) can be synthesized from, for example, a compound having a cyclohexanol structure, as described in JP-48029899 A, 58172387 A and 2000169399 A. As is apparent from the formula (II), the alicyclic olefin compound obtained preferably has double bonds at 3- and 4-positions to substituent X, and the compound having hydroxyl group which is a raw material of the alicyclic olefin compound preferably has hydroxyl group at 4-position to substituent X.

The examples of those compounds include a compound containing at least two cyclohexane rings having hydroxyl group bonded thereto in the molecule, and the present invention is particularly effective to dehydration reaction thereof.

Examples of the compound containing at least two cyclohexane rings having hydroxyl group bonded thereto in the molecule include hydrogenated biphenol, dicyclohexanol methane, bis(dimethylcyclohexanol)methane, 1,2-bis(cyclohexanol)ethane, 1,3-bis(cyclohexanol)propane, 1,4-bis(cyclohexanol)butane, 1,5-bis(cyclohexanol)pentane, 1,6-bis(cyclohexanol)hexane, 2,2-bis(cyclohexanol)propane, bis(cyclohexanol)phenylmethane, α,α-bis(4-hydroxycyclohexyl)-4-(4-hydroxy-α,α-dimethylcyclohexyl)-ethylbenzene, 3,3-bis(cyclohexanol)pentane, 5,5-bis(cyclohexanol)heptane, dodecahydrofluorene diol, tris(cyclohexanol)methane, tris(cyclohexanol)ethane, 1,3,3-tris(cyclohexanol)butane, tetrakis(cyclohexanol)ethane, 2,2-bis[4,4'-bis(cyclohexanol)cyclohexyl]propane, bisphenol C hydride (C: cyclohexane) and hydrogenated polyphenol. Those can be used alone or as mixtures of two or more thereof.

The aliphatic percarboxylic acid having low water content is preferably used as an epoxidizing agent that can be used for epoxidation of double bond in the alicyclic olefin compound. The reason for this is that if epoxidation is conducted in the presence of moisture, ring-opening reaction of epoxy group proceeds, and thus yield of an epoxy compound decreases.

For this reason, it is essential for the aliphatic percarboxylic acid to have a water content of 2% by weight or less, preferably 1% by weight or less, more preferably 0.8% by weight or less and most preferably 0.6% by weight or less.

The aliphatic percarboxylic acid having a water content of 2% by weight or less as described in the present invention generally means peracetic acid or the like produced by air oxidation of acetaldehyde or the like. For example, peracetic acid is produced by a method described in German Patent Laid-Open No. 1418465 or JP-54003006 A. The aliphatic percarboxylic acid having a water content of 2% by weight or less may also be produced by synthesizing an aliphatic percarboxylic acid from an aliphatic carboxylic acid using hydrogen peroxide, and then extracting it through distillation or by using a solvent.

The method using air oxidation of acetaldehyde or the like enables a large amount of high concentration aliphatic percarboxylic acid to be synthesized continuously. As a result, the aliphatic percarboxylic acid can substantially be obtained inexpensively.

As aliphatic percarboxylic acids, performic acid, peracetic acid, perisobutyric acid, pertrifluroacetic acid or the like can be used. Of those, peracetic acid is particularly preferable because it is industrially available at low cost and has high stability.

Amount of the aliphatic percarboxylic acid as an epoxidizing agent is not strictly limited, and the optimum amount thereof in each case can be determined in accordance with variable factors such as individual epoxidizing agent used, desired degree of epoxidation, or individual material to be epoxidized. In the case where a compound having a large number of epoxy groups in the molecule is used, the epoxidizing agent is preferably added in an equimolar amount or more to olefin group. However, from the economical viewpoint and considering the problem of a side-reaction as described hereinafter, the amount of the epoxidizing agent exceeding 2 times by mole is generally disadvantageous. In the case of peracetic acid, the amount is preferably 1 to 1.5 times by mole.

Epoxidation reaction is conducted using or not using an inert solvent, or by controlling reaction temperature, depending on an apparatus or physical properties of a raw material.

The inert solvent can be used to decrease viscosity of a raw material or to stabilize an epoxidizing agent by means of dilution. In the case of peracetic acid, aromatic compounds, esters or the like can be used.

Particularly preferable solvents are hexane, cyclohexane, toluene, ethyl acetate and methyl acetate.

A reaction temperature range that can be used is determined by reactivity of the epoxidizing agent to be used. In general, the reaction temperature is 0° C. or higher and 100° C. or lower. In the case of peracetic acid that is a preferable epoxidizing agent, the reaction temperature is preferably 20 to 70° C. If the reaction temperature is lower than 20° C., reaction proceeds slowly, and if it is higher than 70° C., decomposition of peracetic acid occurs.

Charging molar ratio of the epoxidizing agent to unsaturated bond can be varied according to the purpose, such as, how much of unsaturated bond should be remained.

Special operations need not to be performed to a reaction mixture. For example, the reaction mixture may be simply stirred for 1 to 5 hours. The epoxidized product obtained can be isolated by an appropriate method such as a method of precipitating it in a poor solvent, a method of introducing the epoxidized product in hot water while stirring it and removing a solvent by distillation, and a direct desolvation method.

The alicyclic epoxy compound (A) represented by the above formula (I) produced by the production method of the invention I can produce intermediates for use in various coatings, inks, adhesives, sealants, moldings or other articles using those, by homopolymerization, copolymerization or reacting with other compound.

Examples of the end uses of the alicyclic epoxy compound (A) produced by the production method of the invention I include acid scavengers, coatings for furniture, coatings for decoration, cans for beverages or other can coatings, adhesives, automobile undercoats, sealers, finish coatings, inks for character information or image information, sealants for electronic parts, printing plates or photoresists suitable for development of printed circuit boards, cast printing rolls, glasses mainly containing unsaturated polyester and styrene, molded blends reinforced with carbon, graphite or other fibers or molded articles made by sheet forming blend, solvents, flame retardants, intermediates for producing other compounds useful for various end uses including medicines and medical goods.

Further, the alicyclic epoxy compound (A) produced by the production method of the invention I can also possess heat resistance, transparency and good dielectric properties, which are the characteristics of a cured resin using a compound having an alicyclic skeleton.

Hereinafter, the invention II is described in detail below.

The invention II relates to a liquid epoxy resin composition using the alicyclic epoxy compound (A) represented by the above formula (I) as a preferable alicyclic epoxy resin, and a photosemiconductor device in which a photosemiconductor element is encapsulated with the liquid epoxy resin composition. Each component in the composition is described below.

The alicyclic epoxy compound (A) used in the invention II is the compound as described in detail in the invention I, and is generally a liquid at ordinary temperature (25° C.).

The liquid epoxy resin composition in the invention II contains the alicyclic epoxy compound (A) in an amount of 100 to 20% by weight.

As the alicyclic epoxy compound (A), compounds produced by the production method as described in the invention I in detail are preferably used, but compounds produced by other production method can also be used. Further, commercially available products can be also used.

The following compounds can be used together as the alicyclic epoxy resin other than the alicyclic epoxy compound (A): 3,4-epoxycyclohexylmethyl-3',4'-epoxycyclohexane carboxylate 3,4-epoxy-6-methylcyclohexylmethyl-3,4-epoxy-6-methylcyclo-hexane carboxylate; bis(3,4-epoxycyclohexyl)adipate, vinyl-cyclohexene monoepoxide; limonene diepoxide and the like.

The following reactive diluent may be used together with the above epoxy compounds. As low-viscosity cycloalkylene glycol diglycidyl ether, for example, low-viscosity cycloalkylene glycol diglycidyl ether having a viscosity of 100 cps or lower at 25° C. is used. Examples of the cycloalkyleneglycol diglycidyl ether include cyclohexanedimethanol diglycidyl ether and cyclohexanediol diglycidyl ether.

Glycidyl type epoxy resins such as liquid bisphenol A or F, hydrogenated bisphenol A type epoxy resins, glycidyl amine type epoxy resins and the like may also be used.

Even a solid epoxy resin can be used so long as an epoxy resin having such a solid epoxy resin blended therewith has a viscosity of 40,000 cp or lower at 45° C. Examples of the solid epoxy resin that can be used include solid bisphenol epoxy resins, novolak type epoxy resins, glycidyl esters, triglycidyl isocyanurates and EHPE-3150 (a product of Daicel Chemical Industries, Ltd.)

Those epoxy resins can be used alone or as mixtures of two or more thereof.

Curing Agent (C)

As an acid anhydride for use as a curing agent (C) in the invention II, any compound can be selected from compounds generally used as a curing agent for an epoxy resin.

The acid anhydride for use in the invention II is preferably liquid at ordinary temperature. Specific examples of the acid anhydride include methyltetrahydrophthalic anhydride, methylhexahydrophthalic anhydride, dodecenylsuccinic anhydride and methylendomethylenetetrahydrophthalic anhydride.

Acid anhydrides that are solid at ordinary temperature, such as phthalic anhydride, tetrahydrophthalic anhydride, hexahydrophthalic anhydride and methylcyclohexenedicarboxylic anhydride, can be used in an amount such that it does not adversely affect impregnation property of the liquid epoxy resin composition of the invention II. In the case where an acid anhydride that is solid at ordinary temperature is used, it is preferable that the solid acid anhydride is dissolved in an acid anhydride that is liquid at ordinary temperature, and is used as a mixture that is liquid at ordinary temperature.

It is sufficient for an amount of the acid anhydride added to be an amount effective for exhibiting the effects as the curing agent (C). Although the amount of acid anhydride is not particularly limited, the acid anhydride is preferably used in a proportion such that the amount thereof is 0.5 to 1.5 acid anhydride equivalent based on one equivalent of epoxy group in the epoxy resin component.

Curing Accelerator (D)

The curing accelerator (D) in the invention II mainly comprises diazabicycloundecene-based curing accelerator, and it is necessary that the diazabicycloundecene-based curing accelerator comprises at least 50% by weight of the entire curing accelerator (C). If the proportion of the diazabicycloundecene-based curing accelerator is less than 50% by weight, pot life cannot sufficiently be prolonged. In order to obtain a sufficient pot life, it is preferable that the proportion of the diazabicycloundecene-based curing accelerator is 70% by weight or more.

Examples of the diazabicycloundecene-based curing accelerator include 1,8-diazabicyclo[5.4.0]undecene-7 and a salt thereof. In particular, octylate of 1,8-diazabicyclo[5.4.0] undecene-7 is preferable. The curing accelerator (D) may be composed of the diazabicycloundecene-based curing accelerator alone or may be a mixture of the diazabicycloundecene-based curing accelerator and up to 50% by weight of a curing accelerator for other epoxy resins such as tertiary amine hardening accelerators and phosphorus-based curing accelerators (e.g., triphenylphosphine) that are commonly used.

The curing accelerator (D) is used in an amount of 0.3 to 10 parts by weight based on 100 parts by weight of the epoxy resin. If the amount of the curing accelerator (D) is less than 0.3 part by weight, curing acceleration effect is insufficient, and on the other hand, if the amount thereof exceeds 10 parts by weight, pot life is shortened disadvantageously. Therefore, from the view points of curing acceleration and pot life, the particularly preferable amount of the curing accelerator (D) is 1 to 5 parts by weight based on 100 parts by weight of the epoxy resin component.

The curing accelerator (D) is a compound having a function of promoting a curing reaction when the epoxy resin is hardened by an acid anhydride.

Other examples of the curing accelerator (D) used in the invention II include: tertiary amines such as benzyldimethyl amine and 2,4,6-tris(dimethylaminomethyl)phenol; imidazoles such as 2-ethyl-4-methylimidazole and 1-cyanoethyl-2-ethyl-4-methylimidazole; organic phosphine compounds such as triphenylphosphine; tertiary amine salts; quaternary ammonium salts; phosphonium salts; and metal salts such as tin octylate, that are known compounds.

The amount of the curing accelerator (D) added is preferably 1 to 10 parts by weight based on 100 parts by weight of the epoxy resin.

Cationic Polymerization Initiator (E)

Cationic polymerization initiator (E) may be used as a curing agent in the invention III. The cationic polymerization initiator (E) is a compound which releases a substance initiating a polymerization by heating. The initiator is added in an amount of 0.05 to 5 parts by weight, preferably 0.1 to 3 parts by weight, based on 100 parts by weight of the epoxy resin. When the initiator is added within the above range, a cured product having excellent heat resistance, transparency, weatherability and the like can be obtained.

Examples of the cationic polymerization initiator (E) include aryl diazonium salts such as PP-33 from Asahi Denka Industry Co.; aryl iodonium salts; aryl sulfonium salts such as FC-509 from 3M, UVE 1014 from G.E., UVI-6974, UVI-6970, UVI-6990 and UVI-6950 from Union Carbide, SP-170 and SP-150 from Asahi Denka Industry Co., SI060L, SI-80L and SI-100L from Sanshin Chemical Industry Co., and allene-ion complexes such as CG-24-61 from Ciba Geigy AG.

Further examples of the cationic polymerization initiator (E) include chelate compounds of metal (such as aluminum or titanium) and acetates or diketones; and chelate compounds including system with silanol or phenols. Examples of aluminum acetylacetonate silanol or phenols include triphenyl silanol and bisphenol S.

Various Additives

Various additives can be added to the liquid epoxy resin composition of the invention II in an amount not adversely affecting viscosity of the liquid epoxy resin composition.

Examples of such additives include silicone or fluorine-based defoamers and silane coupling agents such as γ-glycidoxypropyl trimethoxysilane.

The liquid epoxy resin composition of the invention II provides a cured product having high glass transition temperature and high transparency, and low water absorption, and therefore is suitable for use as a resin composition for photosemiconductor encapsulation.

The liquid epoxy resin composition of the invention II, particularly the epoxy resin composition for photosemiconductor encapsulation, can further contain, optionally, various additives such as fillers, flame retardants, defoamers, coloring materials and silane coupling agents, which are hitherto commonly used in the epoxy resin compositions for photosemiconductor encapsulation.

Hereinafter, the invention III is described in detail below.

The invention III relates to an ultraviolet rays-curable can-coating composition containing an alicyclic epoxy resin compound (A) represented by the formula (I) as an essential component, and to a process of producing a coated metal can using the composition.

Each component in the ultraviolet rays-curable can-coating composition of the invention III is described below.

The alicyclic epoxy compound (A) used in the invention III is preferably a compound produced by the method as described in detail in the invention I. The alicyclic epoxy compound (A) is generally liquid at ordinary temperature (250).

As the above alicyclic epoxy compound (A), a compound produced by the method as described in detail in the invention I is preferably used, but compounds produced by other methods may also be used. Further, commercially available products can also be used.

As an alicyclic epoxy compound other than the alicyclic epoxy compound (A), for example, a compound having an alicyclic epoxy group in the molecule and having an ester linkage and/or an epoxy compound (B) having a glycidyl group can be used together in an amount of 0 to 80% by weight.

As the compound having an alicyclic epoxy group in the molecule and having an ester linkage and/or the epoxy compound (B) having a glycidyl group, any compound can be used without particular limitation if it is a compound having at least one piece, preferably 1 to 2 pieces, of alicyclic epoxy groups in the molecule.

Specific examples of such a compound include di(3,4-epoxycyclohexyl)adipate, 3,4-epoxycyclohexylmethyl-3',4'-epoxycyclohexane carboxylate, (3,4-epoxy-6-methylcyclohexyl)methyl-3,4-epoxy-6-methylcyclohexane carboxylate, and ethylene-1,2-di(3,4-epoxycyclohexane carboxylic acid) ester. Those compounds can be used alone or as a mixture of two or more thereof. Of the compounds having an alicyclic epoxy group in the molecule, particularly preferable compounds are 3,4-epoxycyclohexylmethyl-3',4'-epoxycyclohexane carboxylate, 3,4-epoxycyclohexylmethyl alcohol, 3,4-epoxycyclohexylethyl trimethoxysilane and compounds represented by the following formula:

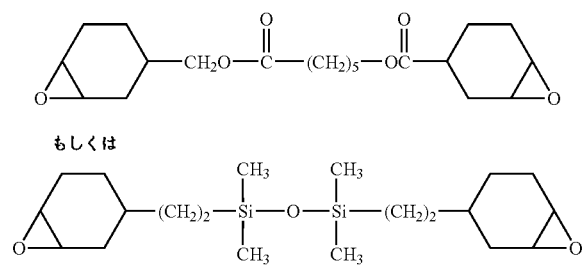

もしくは

In the invention III, compounds having oxetane ring in the molecule can also be used.

The compound having an oxetane ring in the molecule for use in the coating composition of the invention III is a compound having at least one piece, preferably 1 to 15 pieces, more preferably 1 to 4 pieces, of oxetane rings represented as below,

which is capable of undergoing ring-opening polymerization by ultraviolet irradiation in the presence of a cationic polymerization initiator (hereinafter this compound is referred to as "oxetane compound OXE" for simplicity). Examples of such OXE include a compound represented by the following formula (4), and compounds represented by the formulae (10), (11) and (12) shown hereinafter.

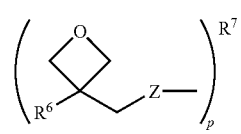

(4)

In the formula (4), $R^6$ represents a hydrogen atom, a fluorine atom, a straight-chain, branched-chain or cyclic alkyl group having 1 to 6 carbon atoms (such as methyl, ethyl, n- or i-propyl, n-, i- or t-butyl, pentyl, hexyl or cyclohexyl group), a straight-chain or branched-chain fluoroalkyl group having 1 to carbon atoms (such as monofluoromethyl, difluoromethyl, trifluoromethyl, 2,2,2-trifluoroethyl, perfluoromethyl, perfluoropropyl, perfluorobutyl or perfluorohexyl), allyl group, aryl group (such as phenyl, naphthyl, tolyl or xylyl group), aralkyl group (such as benzyl or phenethyl group), furyl group or thienyl group; $R^7$ has the number of valency corresponding to the value of p and represents hydrogen atom or an organic mono- to tetravalent group; Z represents oxygen atom or sulfur atom; and p is an integer of 1 to 4.

Examples of the mono- to tetravalent organic group that may be represented by $R^7$ include straight-chain, branched-chain or cyclic mono- to tetravalent hydrocarbon groups having 1 to 30 carbon atoms, which may contain at least one hetero atom selected from O, S, N and F and/or a siloxane linkage.

More specifically, examples of the monovalent group that may be represented by $R^7$ include: a straight-chain, branched-chain or cyclic alkyl group having 1 to 6 carbon atoms (such as methyl, ethyl, n- or i-propyl, n-, i or t-butyl, pentyl, hexyl or cyclohexyl group); a straight-chain or branched-chain alkoxyalkyl group having 1 to 6 carbon atoms (such as methoxyethyl, ethoxyethyl, butoxyethyl or ethoxymethyl group); a straight-chain or branched chain fluoroalkyl group having 1 to 6 carbon atoms (such as monofluoromethyl, difluoromethyl, trifluoromethyl, 2,2,2-trifluoroethyl, perfluoromethyl, perfluoropropyl, perfluorobutyl or perfluorohexyl group); allyl group; aryl group (such as phenyl, naphthyl, tolyl or xylyl group); aralkyl group (such as benzyl or phenethyl group); furyl group; thienyl group; and an epoxy group-containing group (such as glycidyl or 3,4-epoxycyclohexylmethyl group).

Examples of the divalent group that may be represented by $R^7$ include: a straight-chain, branched chain or cyclic alkylene group (in particular, an alkylene group having 1 to 15 carbon atoms such as methylene, ethylene, 1,2- or 1,3-propylene, butylene or cyclohexylene group); a (polylalkyleneoxy) group having 4 to 30, preferably 4 to 8, carbon atoms (such as poly(oxyethylene) or poly(propyleneoxy) group); phenylene group; xylilene group; groups represented by the following formulae (5) and (6):

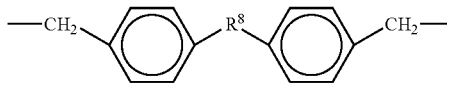

(wherein $R^8$ represents O, S, $CH_2$, NH, SO, $SO_2$, $C(CF_3)_2$ or $C(CH_3)_2$)

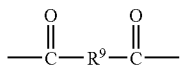

(wherein $R^9$ represents an alkylene group having 1 to 6 carbon atoms, an arylene group or a direct linkage);

and a group having 2 to 30, preferably 2 to 6, carbon atoms, in which alkylene group and alkylene group are linked with (poly)siloxane chain (such as a group wherein the alkylene group is ethylene or propylene group, and the (poly)siloxane chain has a molecular weight of 130 to 15,000, preferably 130 to 500, which is preferably a group represented by the following formula (7)):

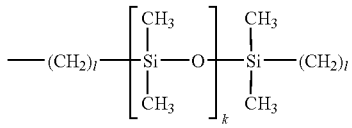

(wherein k is an integer of 1 to 6, and l is 2 or 3.)

Examples of tri- or tetravalent group which $R^7$ may represent include groups represented by the following formulae (8) to (11):

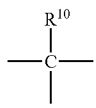

wherein $R^{10}$ represents an alkyl group having 1 to 6 carbon atoms, such as ethyl group;

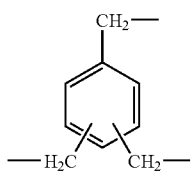

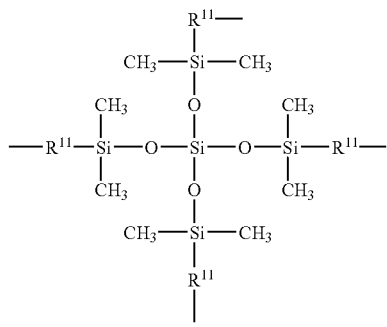

wherein four $R^{11}$ are the same or different, and each represents an alkylene group having 1 to 6 carbon atoms, such as ethylene;

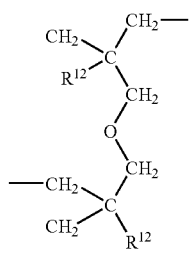

wherein two $R^{12}$ are the same or different, and each represents a hydrogen atom, a fluorine atom, an alkyl group having 1 to 6 carbon atoms, a fluoroalkyl group having 1 to 6 carbon atoms, allyl group, aryl group, furyl group or thienyl group.

The mono- to tetravalent organic groups which $R^7$ may represents is preferably mono- or divalent group (that is, p is preferably 1 or 2). Of those groups, preferred are an alkyl group having 1 to 6 carbon atoms such as methyl, ethyl, propyl, butyl or hexyl; allyl group; glycidyl group; vinyl group; an alkoxyalkyl group having 1 to 6 carbon atoms such as ethoxyethyl and methoxyethyl; benzyl group; an alkylene group having 1 to 6 carbon atoms such as methylene, ethylene, propylene, butylene and hexylene; p-xylylene group; and a group represented by the following formula:

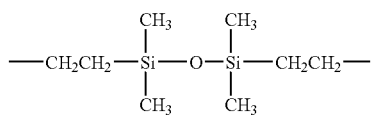

Further in the formula (4), $R^6$ is preferably hydrogen atom; an alkyl group having 1 to 6 carbon atoms such as methyl, ethyl, propyl, butyl or hexyl; or allyl group. Of those, hydrogen atom, methyl or ethyl is more preferable.

The compound (OXE) having at least one oxetane ring in the molecule is preferably a compound having at least one oxetane ring and hydroxyl group, respectively, in the molecule (OXE-1) and a compound having at least two oxetane rings, or having oxetane ring and epoxy group, in the molecule.

Examples of the oxetane compound (OXE-1) include a compound of the formula (4) wherein p is 1 and $R^7$ is hydrogen atom, particularly a compound represented by the following formula (4-1):

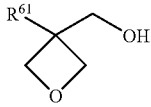
(4-1)

wherein $R^{61}$ represents a hydrogen atom, a fluorine atom, a straight-chain or branched-chain alkyl group having 1 to 6 carbon atoms, a straight-chain or branched-chain fluoroalkyl group having 1 to 6 carbon atoms or allyl group.

A representative example of the compound represented, by the formula (4-1) is a compound of the formula (4-1) wherein $R^4$ is ethyl group.

Also, of the oxetane compound (OXE-2), an example of the compound having at least two oxetane rings in the molecule (hereinafter this compound is referred to as "polyoxetane compound") is a compound of the formula (4) wherein p is an integer of 2 to 4. Of those, a compound represented by the following formula (4-2) is particularly preferable.

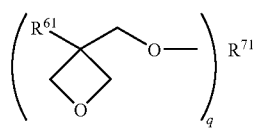
(4-2)

wherein $R^{61}$ is the same as defined above, $R^{71}$ represents di- to tetravalent organic groups as defined for $R^7$ in the formula (4), and q is an integer of 2 to 4.

A representative example of the compound represented by the formula (4-2) is a compound of the formula (4-2) wherein $R^{61}$ is ethyl group, and $R^{71}$ is 1,4-tetramethylene group, dodecamethylene group, o-, m- or p-xylylene group, a group of the formula (6) wherein $R^9$ is ethylene group, and a group of the formula (7).

In addition to the compound represented by the formula (4-2), examples of the polyoxetane compound further include compounds represented by the following formula (12), (13) and (14):

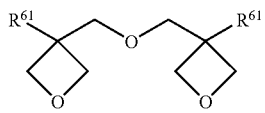
(12)

wherein two $R^{61}$ are the same or different, and are the same as defined above and are preferably ethyl group,

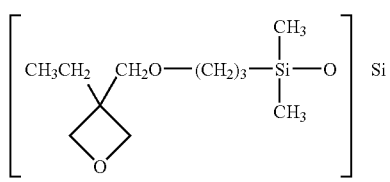
(13)

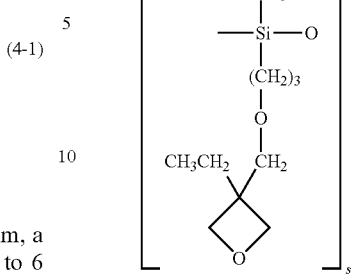
(14)

wherein s is an integer of 25 to 200.

Further, of the oxetane compound (OXE-2), a compound having oxetane ring and epoxy group in the molecule (hereinafter, this compound is referred to as "epoxy group-containing oxetane compound") includes a compound having one oxetane ring and one epoxy group in the molecule and preferably having a molecular weight of less than 1,000. A specific example of such a compound is a compound represented by the following formula (15):

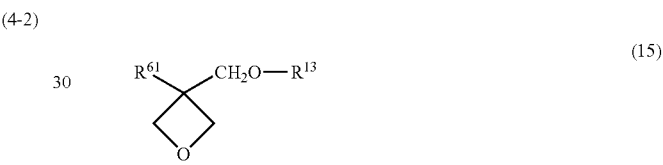
(15)

wherein $R^{13}$ represents epoxy group-containing group, and $R^{61}$ is the same as defined above.

A representative example of the epoxy group-containing oxetane compound is a compound represented by the formula (15) wherein $R^{61}$ is ethyl group and $R^{13}$ is glycidyl group or 3,4-epoxycyclohexylmethyl group.

The oxetane compound (OXE) can be used alone or as a mixture of two or more thereof. Use of a combination of the compound (OXE-1) and the compound (OXE-2) is particularly preferable. Amounts of the compound (OXE-1) and the compound (OXE-2) when used in combination are such that the amount of the compound (OXE-1) used is 1 to 75 parts by weight, preferably 3 to 50 parts by weight, and the amount of the compound (OXE-2) used is 1 to 75 parts by weight, preferably 3 to 50 parts by weight, per 100 parts by weight of the total amount of the epoxy compound (A) and the epoxy compound (B).

Copolymer (F) Containing at Least One Glycidyl Group and/or Alicyclic Epoxy Group in the Molecule Copolymer (F) for use in the coating composition of the invention III is a copolymer having at least one glycidyl group and/or alicyclic epoxy group in the molecule.

As an epoxy group-containing monomer which is a raw material of the copolymer, any polymerizable unsaturated monomer containing epoxy group can be used without specific limitation. Representative examples of the monomer include glycidyl acrylate, glycidyl methacrylate, methylglycidyl acrylate, methylglycidyl methacrylate, allylglycidyl etherandvinylglycidyl ether. Of those, glycidyl acrylate and glycidyl methacryalte are preferably used.

Examples of alicyclic epoxy group-containing monomer which is a raw material of the copolymer include Cyclomer A200 and M100, products of Daicel Chemical Industries, Ltd.

Other monomers copolymerizable with the epoxy group-containing monomer are monomers that are appropriately used, optionally, according to intended performances of the copolymer (F) obtained. Examples of the other monomers include $C_1$-$C_{24}$ aklyl or cycloalkyl esters of acrylic acid or methacrylic acid, such as methyl methacrylate, ethyl methacrylate, methyl acrylate, ethyl acrylate, n-, i- or t-butyl acrylate, n-, i- or t-butyl methacrylate, hexyl acrylate, hexyl methacrylate, octyl acrylate, octyl methacrylate, lauryl acrylate, lauryl methacrylate, stearyl acrylate, stearyl methacrylate, cyclohexyl acrylate or cyclohexyl methacrylate; $C_1$-$C_8$ hydroxyalkyl esters of acrylic acid or methacrylic acid, such as 2-hydroxyethyl acrylate, 2-hydroxyethyl methacrylate, 2-hydroxypropyl acrylate, 2-hydroxypropyl methacrylate, 4-hydroxybutyl acrylate or 4-hydroxybutyl methacrylate; α,β-ethylenically unsaturated carboxylic acids such as acrylic acid, methacrylic acid, maleic acid, itaconic acid or crotonic acid; acrylamides or methacrylamides, such as acryliamide, methacrylamide, N-methyl acrylamide, N-ethyl methacrylamide, diacetone acrylamide, N-methylol acrylamide, N-methylol methacrylamide, N-methoxymethyl acrylamide or N-butoxymethyl acrylamide, or their derivatives; aromatic vinyl monomers such as styrene, vinyltoluene or α-methylstyrene; and other vinyl monomers such as vinyl propionate, vinyl acetate, arylonitrile, methacrylonitrile, vinylpivalate, Beovamonomer (a product of Shell Chemical, vinyl ester of branched fatty acid), and Cylaplane FM0711, FM0721 and FM0725 (products of Chisso Co., polydimethylsiloxane macromonomer having methacryloyl group at the terminals).

The copolymer (F) can be obtained by polymerizing monomer components comprising the epoxy group-containing monomer and optionally other monomers in the presence or absence of a radical polymerization initiator by a known polymerization method, such as solution polymerization, bulk polymerization, emulsion polymerization and suspension polymerization. The copolymer (F) has a number average molecular weight of 1,000 to 100,000, preferably 2,000 to 50,000.

The amount of each monomer component in polymerization of the copolymer (F) is preferably within the following ranges based on 100 parts by weight of the sum of the monomer components.

Epoxy group-containing monomer: 10 to 95 parts by weight, preferably 20 to 80 parts by weight.

Other monomer: 0 to 85 parts by weight, preferably 10 to 70 parts by weight.

Concentration of epoxy group in the copolymer (F) is 0.1 to 7.0 equivalents/kg, preferably 0.2 to 5.0 equivalents/kg.

When polydimethylsioxane macromonomer such as Cylaplane FM0721 (a product of Chisso Co.) is used as the other monomer in the polymerization of the copolymer (F), leveling property of a coating film obtained or lubricating property of a coating film after retort treatment can be improved.

Cationic Polymerization Initiator (G)

Cationic polymerization initiator (G) used in the invention III is a compound that generates cation by ultraviolet irradiation, thereby initiating polymerization. Examples of the cationic polymerization initiator include hexafluoroantimonates, pentafluorohydroxyantimonates, hexafluorophosphates, hexafluoroarsenates and other cationic polymerization initiators, represented by the following formulae (I) to (XV):

(I)

wherein Ar represents aryl group such as phenyl group, and $X^-$ represents $PF_6^-$, $SbF_6^-$ or $AsF_6^-$;

(II)

wherein Ar and $X^-$ are the same as defined above;

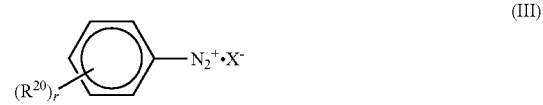

(III)

wherein $R^{20}$ represents an alkyl group having 1 to 12 carbon atoms or an alkoxy group having 1 to 12 carbon atoms, r is an integer of 0 to 3, and $X^-$ is the same as defined above;

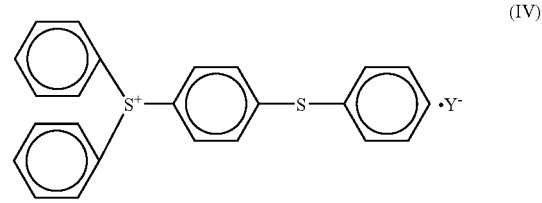

(IV)

wherein $Y^-$ represents $PF_6^-$, $SbF_6^-$, $AsF_6^-$ or $SbF_5(OH)^-$;

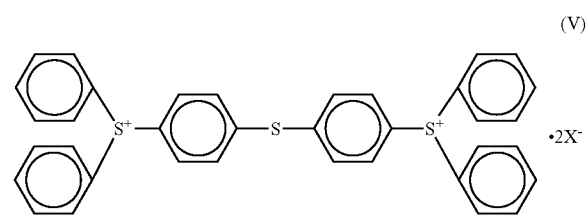

(V)

wherein $X^-$ is the same as defined above;

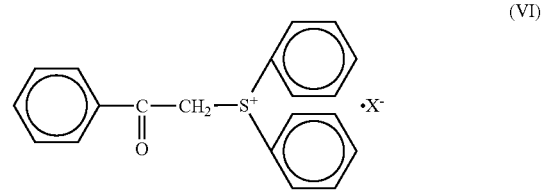

(VI)

wherein $X^-$ is the same as defined above;

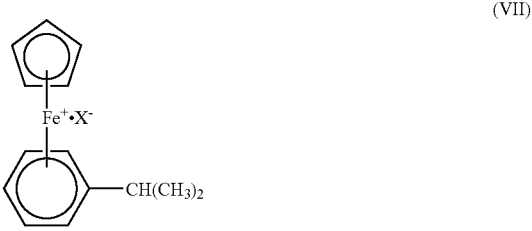

(VII)

wherein $X^-$ is the same as defined above;

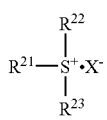
(VIII)

wherein $R^{21}$ represents an aralkyl group having 7 to 15 carbon atoms or an alkenyl group having 3 to 9 carbon atoms, $R^{22}$ represents a hydrocarbon group having 1 to 7 carbon atoms or hydroxyphenyl group, $R^{23}$ represents an alkyl group having 1 to 5 carbon atoms, which may contain oxygen atom or sulfur atom, and $X^-$ is the same as defined above;

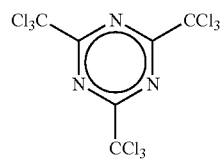
(IX)

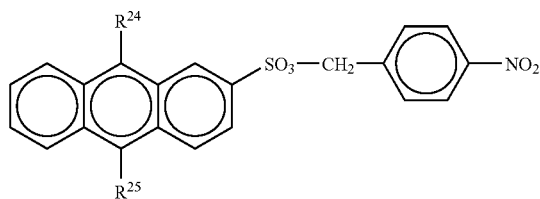
(X)

wherein $R^{24}$ and $R^{25}$ each independently represents an alkyl group having 1 to 12 carbon atoms or an alkoxy group having 1 to 12 carbon atoms;

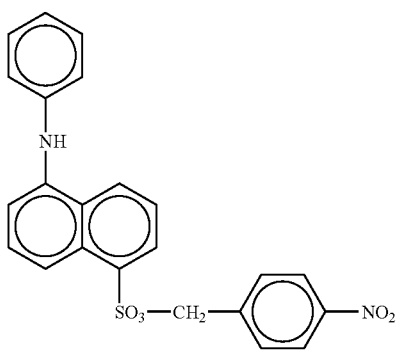
(XI)

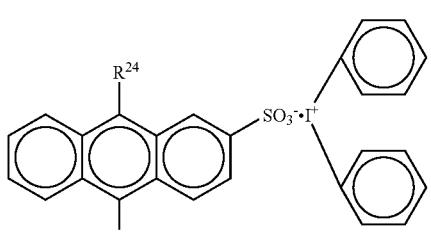
(XII)

wherein $R^{24}$ and $R^{25}$ are the same as defined above.

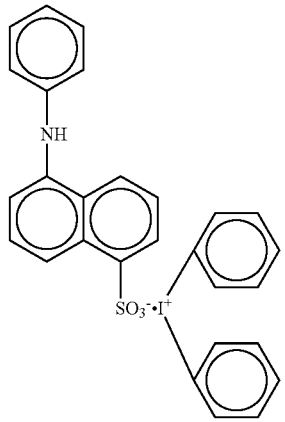
(XIII)

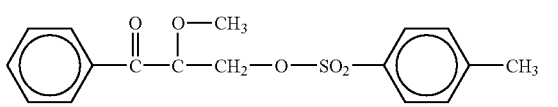
(XIV)

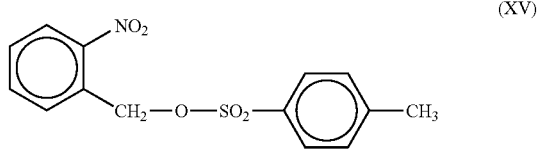
(XV)

As the cationic polymerization initiator (G), commercially available products can also be used, and examples thereof include UVACURE 1591 (a product of UCB, U.S.A.), CD-1010, CD-1011 and CD-1012 (products of Sartomer Co., U.S.A.), IRGACURE 264 (a product of Ciba Geigy AG) and CIT-1682 (a product of Nippon Soda Co.).

Of the above cationic polymerization initiators, compounds having hexafluorophosphate anion ($PF_6^-$) are preferable from the viewpoints of toxicity, general-purpose properties and the like.

The coating composition of the invention III can optionally contain lubricity-imparting agents; sensitizers; pigments or dyes, such as coloring pigment or extender pigment, added in an amount not substantially inhibiting the curing; modifying resins such as polyol resins, phenolic resins, acrylic resins, polyester resins, polyolefin resins, epoxy resins and epoxidized polybutadiene resins; organic resin fine particles; solvents; or the like, in addition to the components (A), (B), (F) and (G) that are essential components.

The lubricity-imparting agent is added for the purpose of improving lubricating property of a coating film obtained, and examples thereof include waxes such as fatty acid ester waxes that are an esterified product of polyol compound and fatty acid, silicone waxes, fluorine waxes, polyolefin waxes, animal waxes or vegetable waxes.

Examples of the polyol compound that is a raw material of the fatty acid ester waxes include ethylene glycol, diethylene glycol, triethylene glycol, tetraethylene glycol, 1,3- or 1,4-butanediol, neopentyl glycol, 1,6-hexanediol, glycerin, di- or more polyglycerin, trimethylpropane, pentaerythritol and dipentaerythritol. Of those, polyol compound having at least three hydroxyl groups in the molecule, and of the polyglycerin, trimethylol propane and pentaerythritol are more preferable.

The fatty acid that is another raw material of the fatty acid ester waxes includes saturated or unsaturated fatty acids, and is preferably a fatty acid having 6 to 32 carbon atoms. Preferred specific examples of the suitable fatty acid include saturated fatty acids such as caprylic acid, pelargonic acid, capric acid, lauric acid, myristic acid, palmitic acid, stearic acid, arachic acid, behenic acid, cerotic acid, montanic acid and melissic acid; and unsaturated fatty acids such as caproleic acid, undecylenic acid, palmitoleic acid, oleic acid, linoleic acid, linolenic acid, eleostearic acid, cetoleic acid, erucic acid, licanic acid ricinoleic acid and arachidonic acid.

The fatty acid ester wax is preferably one in which at least ⅓ of the number of hydroxyl groups in the polyol compound is esterified with fatty acid.

Examples of the silicon wax include BYK-300, BYK-320 and BYK-330 (products of BYK Chemie Co.); Silhouette L-77, Silhouette L-720 and Silhouette L-7602 (products of Nippon Unicar, Ltd.), Paintadd 29, Paintadd 32 and Paintadd M (products of Dow Corning Co.); and Shin-Etsu Silicone KF-96 (a product of Shin-Etsu Chemical Co.). Examples of the fluorine wax include Shamrock Wax SST-1MG, Shamrock Wax SST-3 and shamrock Wax Fluoroslip 231 (products of Shamrock Chemicals CO.), and POLYFLUO 120, 150 and 400 (products of Micropowders CO.).

Examples of the polyolefin wax include Shamrock Wax S-394 and Shamrock Wax S-395(products of Shamrock Chemicals Co.); Hoechst Wax PE-520 and Hoechst Wax PE-521 (products of Hoechst AG); and Mitsui Hi-Wax (a product of Mitsui Chemical Industry Co.). Examples of the animal wax include lanolin and beeswax. Examples of the vegetable wax include carnauba wax and beeswax.

The lubricity-imparting agents can be used alone or as a mixture of two or more thereof. The amount of the lubricity-imparting agent added is generally 10 parts by weight or less, preferably 0.1 to 5 parts by weight, more preferably 0.5 to 3 parts by weight, based on 100 parts by weight of the total amount of the compound (A) having alicyclic epoxy group and not having ester linkage in the molecule and the compound (B) having alicyclic epoxy group and ester linkage in the molecule.

Of the lubricity-imparting agents, the silicon wax is excellent in a lubricity-imparting property before retort treatment after coating and curing are performed, and the fatty acid ester wax is excellent in lubricity-imparting property after retort treatment after coating and curing are performed. Therefore, it is preferable to add at least one kind of wax selected from the silicon wax and fatty acid ester wax. In particular, when 0.01 to 5 parts by weight of the silicon wax and 0.1 to 5 parts by weight of the fatty acid ester wax are used in combination, based on 100 parts by weight of the total amount of the epoxy compound (A) having alicyclic epoxy group and not having ester linkage in the molecule and the compound (B) having alicyclic epoxy group and ester linkage or glycidyl group in the molecule, a coating film having an excellent lubricity-imparting property before and after retort treatment can be obtained.

The sensitizer is added for the purpose of further improving curability by ultraviolet ray, and examples thereof include pyrene, perylene, acridine orange, thioxanthone, 2-chlorothioxanthone and benzoflavin. The sensitizer is used in an amount of generally 10 parts by weight or less, preferably 3 parts by weight or less, based on 100 parts by weight of the total amount of the epoxy compound (A) and the epoxy compound (B).

In the case where the modifying resin is added, the modifying resin is preferably used in an amount of generally 0.1 to 50 parts by weight, preferably 5 to 20 parts by weight, based on 100 parts by weight of the sum of the compound (A) having alicyclic epoxy group and not having ester linkage in the molecule, and the compound having alicyclic epoxy group and ester linkage in the molecule and/or epoxy compound (B) having glycidyl group. Of the modifying resins, epoxidized polybutadiene resin is particularly effective for improving processability and adhesion of a coating film and the like.

The organic resin fine particles preferably have a particle size of 50 to 500 nm, and are, for example, acrylic resin fine particles the inside of which is three-dimensionally crosslinked. Examples of the organic resin fine particles include fine particles obtained by pulverizing an organic polymer; fine particles obtained by drying and pulverizing polymer fine particles which are obtained by emulsion polymerizing in water in the presence of an emulsifier; and fine particles obtained by drying and pulverizing of polymer fine particles which are obtained by dispersion polymerization in an organic solvent in the presence of a polymeric stabilizer. Addition of the organic resin fine particles to the coating composition of the invention III can improve adhesion and processability of a coating film. In the case where the organic resin fine particles are added, the amount thereof is generally 0.1 to 50 parts by weight, preferably 1 to 10 parts by weight, based on 100 parts by weight of the total amount of the epoxy compound (A) and the epoxy compound (B).

Coating Composition

The coating composition of the invention III can be prepared by mixing each component described above, and stirring the resulting mixture so as to obtain a uniform coating composition. For example, the coating composition can be prepared as follows. Each component is mixed, followed by optionally heating (e.g., at about 50° C.), and the resulting mixture is stirred with a dissolver or the like until a uniform coating composition is obtained, for example, by stirring it for about 10 minutes.

In preparing the coating composition, the compound (A) having an alicyclic epoxy group and not having an ester linkage in the molecule, the compound having alicyclic epoxy group and ester linkage in the molecule and/or epoxy compound (B) having glycidyl group, the copolymer (F) and the cationic polymerization initiator (G) are used in the amounts as described below.

The alicyclic epoxy compound (A) can be used in an amount of 10 to 90 parts by weight, preferably 20 to 70 parts by weight, more preferably 30 to 60 parts by weight, and the compound (B) can be used in an amount of 10 to 90 parts by weight, preferably 30 to 80 parts by weight, more preferably 40 to 70 parts by weight, provided that the total amount of the compound (A) having alicyclic epoxy group and not having ester linkage in the molecule, and the compound having alicyclic epoxy group and ester linkage in the molecule and/or epoxy compound (B) having glycidyl group is 100 parts by weight. In the case where the sum of the compounds (A) and (B) is 100 parts by weight, if the amount of the alicyclic epoxy compound (A) is less than 10 parts by weight, a coating composition obtained has poor hardness and poor adhesion. On the other hand, if the amount of the alicyclic epoxy compound (A) exceeds 90 parts by weight, curability and retort resistance of a coating film by ultraviolet irradiation in low irradiation dose deteriorate.

The amount of the copolymer (F) used is generally 1 to 50 parts by weight, preferably 3 to 30 parts by weight, more preferably 5 to 20 parts by weight, based on 100 parts by weight of the total amount of the alicyclic epoxy compound (A) having alicyclic epoxy group and not having ester linkage in the molecule, and the compound having alicyclic epoxy group and ester linkage in the molecule and/or epoxy compound (B) having glycidyl group. If the amount of the copolymer (F) is less than 1 part by weight, hardness of the resulting coating film in hot water after post-heating is poor in the ultraviolet irradiation in low irradiation dose, and adhesiveness of the coating film, hardness of the coating film, and the like deteriorate. On the other hand, if the amount of the copolymer (F) exceeds 50 parts by weight, curability by ultraviolet irradiation in low irradiation dose is particularly poor, and hardness of the resulting coating film and retort resistance decrease.

Further, the amount of the cationic polymerization initiator (G) used is generally 0.01 to 20 parts by weight, preferably 0.1 to 10 parts by weight, more preferably 1 to 5 parts by weight, based on 100 parts by weight of the total amount of the alicyclic epoxy compound (A) having alicyclic epoxy group and not having ester linkage in the molecule, and the compound having alicyclic epoxy group and ester linkage in the molecule and/or epoxy compound (B) having glycidyl group.

The ultraviolet rays-curable can-coating composition of the present invention III has an ultraviolet rays curability. The coating composition can be applied to metal plates that are molded and processed into metal cans made of tinplate, aluminum, tin-free steel, iron, zinc, copper, zinc-plated steel plate, steel plate plated with an alloy comprising zinc and other metal, or the like (chemical treatment such as zinc phosphate treatment and chromate treatment may be applied to these metal plates); resin film-laminated metal plates obtained by laminating on the metal plates mentioned above a resin film such as a polyester resin (such as polyethylene terephthalate), a polyolefin resin (such as polyethylene and polypropylene), a polyamide resin, an epoxy resin, and a polyvinyl chloride resin; or metal cans formed from those metal plates, followed by irradiation with ultraviolet ray, thereby forming a cured coating film. Thickness of the coating film can appropriately be selected depending on the purposes of use, but the dry thickness thereof is generally about 2 to 20 µm, preferably about 2 to 8 µm.

The ultraviolet rays-curable can-coating composition of the invention III can be applied by a coating method such as roll coating, spray coating, brush coating, bar coat coating, roller coating and silk screen printing. In the case where the coating film contains a solvent, a solvent is removed by heating or the like from the coating film after the coating process, and the coating film is then cured with ultraviolet irradiation. Irradiation conditions can appropriately be varied depending on the kind of the coating composition applied, thickness of the coating film formed, or the like. Wavelength of ultraviolet ray irradiated is generally within a range of 200 to 600 nm. Irradiation source having wavelength of high sensitivity can appropriately be selected and used in accordance with the kind or the like of the cationic polymerization initiator used.

Examples of irradiation source of ultraviolet ray include high-pressure mercury lamp, ultrahigh pressure mercury lamp, xenon lamp, carbon-arc, metal halide lamp and sunlight. Irradiation conditions to the coating film are generally such that the amount of radiation is 10 to 1,000 mJ/cm$^2$, preferably 50 to 500 mJ/cm$^2$.

Further, the coating film may be optionally heated after ultraviolet irradiation. This heating makes it possible to reduce unreacted products in the coating film and to relax curability of the coating film by ultraviolet irradiation or strain of the coating film generated by molding and processing. In some cases, hardness or adhesion of the coating film can be improved by the heating. The heating can be conducted under the conditions of atmospheric temperature of 150 to 250° C. for 1 to 30 minutes.

The ultraviolet rays-curable can-coating composition of the invention III contains the alicyclic epoxy compound (A) having alicyclic epoxy group and not having ester linkage in the molecule, the compound having alicyclic epoxy group and ester linkage in the molecule and/or epoxy compound (B) having glycidyl group, and the copolymer (F) as film-forming resin components, and can efficiently be cured by cationic polymerization even by ultraviolet irradiation in low irradiation dose in the presence of the cationic polymerization initiator (G), without requiring facilities such as nitrogen sealing. The coating film obtained from the composition are excellent in film performances, such as processability, adhesiveness, hardness and scratch resistance, which are required even for a thin film as a can coating material. Further, the coating composition can also form a coating film having excellent film appearance and retort resistance.

Therefore, the coating composition of the invention III is particularly suitable for use as a coating material for outer surface of a can.

EXAMPLES

The present invention is described in more detail by reference to the following examples, but the invention should not be limited to those examples.

Unless otherwise indicated, all parts and percents as used herein are based on the weight.

Examples of the Invention I

Production Example 1

10% acetaldehyde-ethyl acetate solution containing cobalt acetate was charged in a 300 ml stainless reactor equipped with an air inlet, a perforated plate for dispersing a gas and a cooling jacket at 114 kg/h, and reaction was conducted at 45° C. while blowing compressed air. The resulting reaction solution contained 10.1% of peracetic acid, 2.2% of acetaldehyde monoperacetate and 2.0% of acetic acid. This solution was charged in a distillation column together with sodium polyphosphate, followed by concentration, thereby obtaining a peracetic acid solution. In the solution, a peracetic acid concentration was 29.1% and water content was 0.47%.

Example I-1

Synthesis of Alicyclic Epoxy Compound (A-1)

36 g of water, 12.0 g of sodium hydrogensulfate, 500 g of isopropylidene-4,4'-dicyclohexanol (a product of Aldrich Chemical Company Inc.) and 500 g of Solvesso 150 (a product of Exxon Chemical) as a solvent were added to a 1 liter flask with a jacket, which is equipped with a stirrer, a cooling tube, a thermometer and a nitrogen inlet, and dehydration reaction was conducted at 100° C.

Reaction was completed at the time when water was no longer distilled off. As a result of analysis of the reaction liquid with gas chromatography, 2,2-bis (3',4'-cyclohexenyl) propane was formed in a yield of 96%. The reaction solution obtained was washed with 500 ml of ion-exchanged water using a separatory funnel. An organic layer was then distilled under reduced pressure to obtain 387.0 g of colorless, transparent liquid 2,2-bis(3',-4'-cyclohexenyl)propane. Purity of the liquid obtained was 96.1%.

100 g of the 2,2-bis(3'-4'-cyclohexenyl)propane and 300 g of ethyl acetate were charged in the same type of a 1 liter flask with a jacket as above. While blowing nitrogen to a gas phase, 307.2 g of an ethyl acetate solution of substantially anhydrous peracetic acid obtained in Production Example 1 (peracetic acid concentration: 29.1%; water content: 0.47%) was added dropwise for about 2 hours so that temperature in the reaction system was 30° C. After completion of the dropwise addition of peracetic acid, the resulting mixture was aged at 30° C. for 3 hours to complete the reaction. The liquid at the completion of the reaction was washed with water at 30° C. and low boiling components were removed under 70° C./20 mmHg to obtain 99.4 g of an epoxy compound. Purity of 2,2-bis(3',4'-epoxycyclohexyl)propane in the epoxy compound was 93.4%.

Properties of the product obtained were oxirane oxygen concentration: 11.3% and viscosity: 3,550 cP (25° C.). Peak originated from inner double bond in the vicinity of δ4.5-5 ppm disappeared in $^1$HNMR analysis, and formation of peak by proton originated from epoxy group was confirmed in the vicinity of δ2.9-3.1 ppm.

Example I-2

Synthesis of Alicyclic Epoxy Compound (A-2)

300 g of 4,4'-dicyclohexanolmethane, 600 g of toluene, 3 g of paratoluenesulfonic acid were added to a 1 liter flask with a jacket, which is equipped with a stirrer, a cooling tube, a thermometer and a nitrogen inlet, and dehydration reaction was conducted at 110° C.

Reaction was completed at the time when water was no longer distilled off. As a result of analysis of the reaction liquid with gas chromatography, di(3,4-cyclohexenyl)methane was formed in a yield of 96%. The reaction solution obtained was washed with 500 ml of ion-exchanged water using a separatory funnel. An organic layer was then distilled under reduced pressure to obtain 269 g of colorless, transparent liquid di(3-4-cyclohexenyl)methane.

100 g of the di(3-4-cyclohexenyl)methane and 200 g of ethyl acetate were charged in the same type of a 1 liter flask with a jacket as in Example I-1. While blowing nitrogen to a gas phase, 276.2 g of an ethyl acetate solution of substantially anhydrous peracetic acid obtained in Production Example 1 (peracetic acid concentration: 29.1%) was added dropwise for about 3 hours so that temperature in the reaction system was 25° C. After completion of the dropwise addition of peracetic acid, the resulting mixture was aged at 30° C. for 4 hours to complete the reaction. The reacted liquid was washed with water at 30° C. and low boiling components were removed under 70° C./30 mmHg to obtain 106.4 g of an epoxy compound. Purity of di (3,4-epoxycyclohexyl)methane in the epoxy compound was 91.8%.

Properties of the product obtained were oxirane oxygen concentration: 13.8% and viscosity: 2,590 cP (25° C.). Peak originated from double bond in the vicinity of δ4.5-5 disappeared in $^1$HNMR analysis, and formation of peak by proton originated from epoxy group was confirmed in the vicinity of δ2.9-3.3.

Example I-3

Except that 400 g of hydrogenated bisphenol sulfone (that is, 4,4'-dicyclohexanol sulfone) and 500 g of Solvesso 150 (a product of Exxon Chemical) as a solvent were used, the reaction was conducted in the same manner as in Example I-1 to obtain 330 g of di(3,4-cyclohexenyl)sulfone. Purity thereof was 92.2%.

100 g of the reacted product and 300 g of ethyl acetate were charged in the same type of a 1 liter flask with a jacket as above. While blowing nitrogen to a gas phase, 242.7 g of an ethyl acetate solution of peracetic acid (peracetic acid concentration: 29.1%) was added dropwise for about 2 hours so that temperature in the reaction system was 40° C. After completion of the dropwise addition of peracetic acid, the resulting mixture was aged at 40° C. for 4 hours to complete the reaction. The crude solution was washed with water at 40° C. and low boiling components were removed under 70° C./30 mmHg to obtain 97.0 g of an epoxy compound. Purity of di(3,4-epoxycyclohexyl)sulfone in the epoxy compound was 90.3%.

Properties of the product obtained were oxirane oxygen concentration: 10.8% and viscosity: 6,700 cP (25° C.). Peak originated from double bond in the vicinity of δ4.5-5 disappeared in $^1$HNMR analysis, and formation of peak by proton originated from epoxy group was confirmed in the vicinity of δ2.9-3.3.

Comparative Example I-1

167.7 g of hydrogen peroxide solution with concentration of 60%, 200 g of propionic acid, 0.3 g of sulfuric acid were mixed for 3 hours at 30° C. to synthesize perpropionic acid, and extraction was conducted with 700 g of benzene to obtain perpropiouic acid solution in benzen with concentration of 16.9% (water content: 4.5%).

100 g of 2,2-bis(cyclohexenyl)propane synthesized in Example I-1 was charged in the 1 liter flask with a jacket used in Example I-1. Then, 578.8 g of the aforementioned benzene solution of perpropionic acid was added dropwise for about 1 hour so that temperature in the reaction system becomes 30° C. After completion of the dropwise addition, the resulting mixture was aged at 30° C. for 4 hours. Further, the crude solution was washed with water at 40° C. and low boiling components were removed under 70° C./20 mmHg to obtain 81.8 g of an epoxy compound. Purity of 2,2-(3',4'-epoxycyclohexyl) propane in the epoxy compound was 52%.

Properties of the product obtained were oxirane oxygen concentration: 6.4% and viscosity: 14,560 cP (25° C.). Peak originated from inner double bond in the vicinity of δ4.5-5 disappeared in $^1$HNMR analysis, and formation of peak by proton originated from epoxy group was confirmed in the vicinity of δ2.9-3.3 ppm.

Comparative Example I-2

300 of hydrogen peroxide with concentration of 60%, 280 g of acetic acid were mixed for 3 hours at 30° C. to synthesize peracetic acid, and extraction was conducted with 1,000 g of ethyl acetate to obtain ethyl acetate solution of peracetic acid with concentration of 21.8% (water content: 8.5%).

100 g of 2,2-bis(3',4'-cyclohexenyl)propane synthesized in Example I-1 was charged in the 1 liter flask with a jacket used in Example. Then, 410 g of the aforementioned ethyl acetate solution of peracetic acid with concentration of 21.8% (water content: 8.5%) was added dropwise thereto for about 2 hours so that temperature in the reaction system becomes 30° C. After completion of the dropwise addition, the resulting mixture was aged at 30° C. for 4 hours to complete the reaction. Further, the crude liquid was washed with water at 20° C. and low boiling components were removed under 70° C./20 mmHg to obtain 65.7 g of an epoxy compound. Purity of 2,2-(3',4'-epoxycyclohexyl)propane in the epoxy compound was 37.8%.

Properties of the product obtained were oxirane oxygen concentration: 4.87% and viscosity: 16,000 cP (25° C.). Peak originated from inner double bond in the vicinity of δ4.5-5 disappeared in $^1$HNMR analysis, and formation of peak by proton originated from epoxy group was confirmed in the vicinity of δ2.9-3.3.

According to the invention I, epoxidation of the alicyclic olefin compound can be conducted efficiently and economically using a less toxic solvent.

Examples of the Invention II

It is to be noted that properties of the epoxy resin composition and its cured product in each example of the invention II were evaluated according to the following methods.

Heat Resistance:

A heat-resistant sample composition was thermally cured at 120° C. for 1 hour and then at 160° C. for 3 hours (in Examples II-7 to II-8 and Comparative Example II-2, at 100° C. for 1 hour and then at 160° C. for 3 hours) to obtain a test piece*(length: 10 mm, width: 5 mm, thickness; 5 mm). Glass transition temperature of the test piece obtained was measured with thermomechanical measuring apparatus (TMA) (manufactured by Seiko Instruments Co.). The results obtained were evaluated by the following criteria.

○: 140° C. or higher
Δ: 130° C. or higher and lower than 140° C.
X: lower than 130° C.

Compositions having a glass transition temperature of 140° C. or higher have good heat resistance.

Moisture Resistance:

A moisture resistant sample composition was thermally cured under the same conditions as in the sample for the heat resistance test above to obtain a test piece (length: 50 mm, width: 50 mm, thickness: 3 mm). This test piece was moistened with a pressure cooker (manufactured by Sabai Espec Corp.) under the conditions of 12.0° C., 2 atm: and 50 hours. Weight increase ratio of the test piece after moistening was obtained by the following equation.

Weight increase ratio (%)=$(W-W_0)/W_0 \times 100$ $W_0$ is the weight of the test piece before moistening, and W is the weight of the test piece after moistening. The results obtained were evaluated by the following reference.

⊚: less than 1.2%
○: 1.2% or more and less than 1.5%
Δ: 1.5% or more and less than 2.0%
X: 2.0% or more Test pieces having weight increase ratio of less than 1.5% have good moisture resistance.

Light Transmittance:

An epoxy resin composition was thermally cured at 120° C. for 1 hour and then at 160° C. for 3 hours (in Examples II-7 to II-8 and Comparative Example II-2, at 100° C. for 1 hour and then at 160° C. for 3 hours) and molded to obtain a cured product having a thickness of 1 mm.

Light transmittance of this cured product at a wavelength of 600 nm was measured with a spectrophotometer.

Examples II-1 to II-8

Each component constituting an epoxy resin composition for photosemiconductor encapsulation of the invention II was blended in the respective proportion (parts by weight) shown in Table II-1, and uniformly mixed.

The alicyclic epoxy compound (A-1) produced in Example I-1 was used in Examples II-1, II-2, II-5, II-6 and II-7.

Further, the alicyclic epoxy compound (A-2) produced in Example I-2 was used in Examples II-3, II-4 and II-8.

Comparative Examples II-1 to II-2

Pot life and an impregnation property of each composition obtained by blending the respective components in the proportions (parts by weight) shown in Table II-1 were measured in the same manner as in the Examples. The results obtained are shown in Table II-1.

Further, each composition was cured in the same manner as in the Examples, and heat resistance, moisture resistance and light transmittance of the resulting cured product were measured in the same manners as in the Examples. The results obtained are shown in Table II-2.

The alicyclic epoxy compound (A-1) produced in Example I-1 was used in Comparative Example II-1.

Further, the alicyclic epoxy compound (A-2) produced in Example I-2 was used in Comparative Example II-2.

TABLE II-1

|  | Example II | | | | | | | | Comparative Example II | |
|---|---|---|---|---|---|---|---|---|---|---|
|  | -1 | -2 | -3 | -4 | -5 | -6 | -7 | -8 | -1 | -2 |
| Compound (A-1) produced in Example I-1 | 90 | 85 |  |  | 40 | 40 | 50 |  | 10 |  |
| Compound (A-2) produced in Example I-2 |  |  | 60 | 30 |  |  |  | 40 |  | 15 |
| CEL-2021P | 10 |  | 20 | 50 |  | 40 | 50 | 40 | 80 |  |
| CEL-3000 |  | 5 |  |  |  |  |  |  |  |  |
| EHPE-3150 |  |  | 20 | 20 |  |  |  |  |  |  |
| TEPIC |  |  |  |  | 30 |  |  |  |  |  |
| Epikote 828 |  | 15 |  |  | 30 | 20 |  | 20 |  | 85 |
| Ethylene glycol | 2 | 2 | 2 | 2 | 2 | 2 |  |  | 2 |  |
| MH-700 | 96.6 | 124.9 | 150.8 | 98.1 | 127.1 | 140.6 |  |  | 119.8 |  |
| DBU | 1 | 1.5 | 1 | 1 | 1.5 | 1 |  |  | 1.5 |  |
| SI-100 L |  |  |  |  |  |  |  | 2 |  |  |
| Al(ACAC)$_3$ |  |  |  |  |  |  | 1 |  |  | 1 |

(1) Celloxide 2021P (trade name) (CEL-2021P): a product of Daicel Chemical Industries, Ltd., 3,4-epoxycyclohexylmethyl-3',4'-epoxycyclohexane carboxylate, epoxy equivalent: 134

(2) Celloxide 3000 (tradename) (CEL-3000): a product of Daicel Chemical Industries, Ltd., limonene diepoxide, epoxy equivalent:

(3.) EHPE-3150: a product of Daicel Chemical Industries, Ltd., an alicyclic epoxy resin, epoxy equivalent: 168

(4) Triglycidyl isocyanurate (trade name) TEPIC: a product of Nissan Chemical Co.

(5) Epikote 828 (trade name): a product of Yuka Shell Epoxy Co., a bisphenol A type epoxy resin, liquid at 25° C., epoxy equivalent: 187

(6) Methylhexahydrophthalic anhydride (trade name) MH-700: a product of Shin-Nippon Rika Co.

(7) 1,8-diazabicyclo[5.4.0]undecene-7 (DBU): a product of Wako Pure Chemical Industries, Co.

(8) Sulfonium salt type cationic curing catalyst (trade name) SI-100L: a product of Sanshin Kagaku Co.

(9) Aluminum trisacetyl acetonate (Al(AcAc)$_3$): a product of Daicel Chemical Industries, Ltd.

TABLE II-2

| | Evaluation Result | | | | | | | | | |
|---|---|---|---|---|---|---|---|---|---|---|
| | Example II | | | | | | | | Comparative Example II | |
| | −1 | −2 | −3 | −4 | −5 | −6 | −7 | −8 | −1 | −2 |
| Heat resistance(° C.) | 148 | 142 | 155 | 151 | 146 | 141 | 144 | 141 | 152 | 129 |
| Moisture resistance | ◎ | ◎ | ○ | ◎ | ◎ | ◎ | ◎ | ◎ | Δ | ○ |
| Light transmittance | 91.8 | 88.9 | 93.8 | 89.1 | 95.7 | 91.1 | 93.5 | 90.3 | 90.1 | 72.1 |

The epoxy resin composition for photosemiconductor encapsulation of the invention II can provide a cured product having excellent heat and moisture resistance and transparency.

Example of the Invention III

Production of Copolymer (F) Having at Least One Epoxy Group in Molecule

Production Example III-1

500 parts of toluene was charged in a flask equipped with a stirrer and a cooler, and heated to 95° C. while stirring. While maintaining the temperature at 95° C., a mixture in which 150 parts of glycidyl methacrylate, 250 parts of n-butyl methacrylate and 50 parts of 2,2'-azobisisobutyronitrile were mixed together and dissolved in advance was added dropwise into the flask for 4 hours. After conducting polymerization, toluene was removed by distillation under reduced pressure to obtain a copolymer (F).

The copolymer (F) obtained had a number average molecular weight of about 2,500 and an oxirane oxygen concentration of 1.4%.

Production Examples III-2 to III-3

Various copolymers were obtained in the same manner as in Production Example III-1 except that composition of a mixture added dropwise was changed as shown in Table III-1 below. Number average molecular weight, oxetane ring concentration and glycidyl group concentration of the copolymers obtained are shown in Table III-1 below. Amount of each component in Table III-1 is parts by weight.

TABLE III-1

| | Production Example | | |
|---|---|---|---|
| | III-1 | III-2 | III-3 |
| GMA[1] | 100 | 200 | |
| CYMA-200[2] | | | 150 |
| n-BMA[3] | 150 | 100 | 200 |
| MMA | 200 | 250 | 150 |
| BA | 200 | 150 | 100 |
| HEMA | 50 | | |
| AIBN[4] | 50 | 50 | 50 |

TABLE III-1-continued

| | Production Example | | |
|---|---|---|---|
| | III-1 | III-2 | III-3 |
| Number average molecular weight | 5000 | 3000 | 4500 |
| Oxirane oxygen concentration | 1.4 | 2.7 | 1.8 |

[1]GMA: glycidyl methacrylate
[2]CYMA-200: epoxycyclohexylmethyl acrylate, trade name: Cyclomer A-200, a product of Daicel Chemical Industries, Ltd.
[3]n-BMA: n-butyl methacrylate
[4]AIBN: 2,2'-azobisisobutyronitrile
[5]HEMA: 2-hydroxyethyl methacrylate Examples III-1 to III-7 and Comparative Examples III-1 to III-2

3,4-epoxycyclohexylmethyl-3',4'-epoxycyclohexane carboxylate (shown as CEL-2021P in Table III-2), 3-ethyl-3-hydroxymethyl oxetane (shown as OXE in Table III-2), a compound represented by the formula (12) wherein all $R^{61}$ are ethyl groups (shown as E-DOA in Table III-2), a copolymer obtained in each Production Example, UVACURE 1591 (a product of UCB, U.S.A., a cationic photopolymerization initiator having PF6−), 1 part of a fatty acid ester wax obtained by reacting 1 mole of decaglycerin ether (having 12 hydroxyl groups in one molecule) which is a polyglycerin having a degree of polymerization of 10, with 10 moles of lauric acid, and 0.2 part of Paintadd M (a product of Dow Corning Co., a silicon wax) were blended. The resulting blend was stirred for 20 minutes while maintaining the temperature at 50° C., to obtain an ultraviolet rays-curable can-coating composition.

In Examples III-1, III-2, III-4, and III-5, the alicyclic epoxy compound (A-1) produced in Example I-1 was used.

In Examples III-3, III-6, and III-7, the alicyclic epoxy compound (A-2) produced in Example I-2 was used.

In Comparative Examples III-1 and III-2, neither of the alicyclic epoxy compound (A-1) nor the alicyclic epoxy compound (A-2) was used.

TABLE III-2

|  | Example III | | | | | | | Comparative Example III | |
|---|---|---|---|---|---|---|---|---|---|
|  | -1 | -2 | -3 | -4 | -5 | -6 | -7 | -1 | -2 |
| E-DOA[1] | 60 | 75 |  | 20 | 45 |  |  |  |  |
| E-DOA-f[2] |  |  | 30 |  |  | 80 | 15 |  |  |
| CEL-2021P[3] | 40 | 15 | 40 | 70 |  |  | 40 | 30 | 45 |
| CEL3000[4] |  | 10 |  | 15 | 10 | 15 |  | 15 | 5 |
| OXE[5] |  |  | 15 |  | 10 |  | 30 | 10 | 10 |
| Production Example 1 | 30 | 20 |  |  | 50 |  | 40 |  |  |
| Production Example 2 |  |  | 25 |  |  | 20 |  | 40 |  |
| production Example 3 |  |  |  | 40 |  |  |  |  | 40 |
| Fatty acid ester wax | 1 | 1 | 1 | 1 | 1 | 1 | 1 | 1 | 1 |
| UVACURE-1951[6] | 7 | 6 | 7 | 8 | 6 | 8.5 | 6 | 6 | 7 |

[1]E-DOA: alicyclic epoxy compound (A-1) synthesized in Example I-1
[2]E-DOA-f: epoxy compound (A-2) synthesized in Example I-2
[3]CEL-2021P: 3,4-epoxycyclohexylmethyl-3',4'-epoxycyclohexane carboxylate (a product of Daicel Chemical Industries, Ltd.)
[4]CEL-3000: 1,2,8,9-diepoxylimonene (a product of Daicel Chemical Industries, Ltd.)
[5]OXE: 3-ethyl-3-hydroxymethyl oxetane (a product of Ube Industries Co.)
[6]UVACURE-1591: sulfonium salt type cationic catalyst (a product of Daicel-UCB Co.)

Preparation of Coated Test Plate:

Each of the coating compositions obtained in Examples III-1 to III-7 and Comparative Examples III-1 to III-2 was applied to a tin-free steel plate (TFS) having a thickness of 0.20 mm, and a PET steel plate composed of a tin-free steel plate having a thickness of 0.20 mm having thermo-compression bonded thereto a homo PET (polyethylene terephthalate) having a film thickness of 12 μm, in a dry thickness of 5 μm, and the coated plate was irradiated with ultraviolet ray by using a high pressure mercury vapor lamp (160 W/cm) placed at a distance of 15 cm from the coated plate so that energy dose becomes 80 mJ/cm$^2$ to thereby cure the coating film, thereby obtaining a coated test plate.

Each coated test plate obtained was subjected to the test based on the following test methods. All of the tests were conducted at 20° C.

Test Methods:

Pencil hardness: Coating film of the coated test plate was subjected to pencil scratch test as defined in JIS K-5400, 8.4.2 (1990). Evaluation was made by a tear method.

Impact resistance (Du Pon't type): Falling weight having a diameter on point of impact of ⅜ inch and a weight of 500 g was fallen on a surface on the coated test plate opposite to the coated film from a height of 30 cm using a Du Pon't type impact tester according to JIS K-5400, 8.3.2 (1990) to conduct impact processing. The processed portion was observed with a microscope, and evaluated by the following criteria.

◉: Cracks and peeling of a coating film are not observed at all.
○: Cracks are slightly observed, but peeling of a coating film is not observed.
Δ: Considerable cracks are observed, but peeling of a coating film is not observed.
X: Peeling of a coating film is observed.

Adhesion: 100 squares of 1.5 mm×1.5 mm are formed on a coated surface of a coated test plate according to a cross-cut tape method as defined by JIS K-5400, 8.5.2 (1990). An adhesive cellophane tape is adhered on the coated surface having 100 squares. After rapidly peeling off the tape from the coated surface, the state of the squares is evaluated by the following criteria.

◉: Peeling of squares is not observed at all.
○: Edge portions of squares are slightly peeled.
Δ: Edge portions and other portions are slightly peeled.
X: Considerable peeling is observed.

Hardness in hot water: A coated test plate was heated at 200° C. for 1 minutes, and then dipped in a 80° C. hot water for 10 minutes. Pencil hardness of the coated test plate was measured in the 80° C. hot water.

Evaluation was conducted by a tear method as defined in JIS K-5400, 8.4.2 (1990).

Further, according to the method as described below, leveling test was conducted on each coating composition obtained in Examples III-1 to III-7 and Comparative Examples III-1 to III-2.

Leveling property: Each coating composition was applied onto a PET steel plate with a roll coat method (natural coating) in a dry film thickness of 5 μm. Ultraviolet irradiation is conducted under the condition such that the process of from the coating to the ultraviolet irradiation takes 0.5 second, to thereby cure the coating film, and the coated surface at that time is visually evaluated. Evaluation was conducted by the following criteria.

◉: Excellent smoothness, with no roll traces being observed on a coated surface.
○: Good smoothness, with only slight roll traces being observed on a coated surface.
Δ: Considerably poor smoothness, with considerable roll traces being observed on a coated surface.
X: Extremely poor smoothness, with very noticeable roll traces being observed on a coated surface.

Test Results:

The results of the above test are shown in Table III-3 below

TABLE III-3

Raw material: TFS

|  | Example III | | | | | | | Comparative Example III | |
|---|---|---|---|---|---|---|---|---|---|
|  | -1 | -2 | -3 | -4 | -5 | -6 | -7 | -1 | -2 |
| Pencil hardness | 2H | 2H | 2H | 2H | 2H | H | 2H | HB | H |
| Impact resistance | ◉ | ◉ | ○ | ◉ | ○ | ◉ | ○ | Δ | Δ |
| Adhesion | ◉ | ○ | ◉ | ○ | ○ | ○ | ◉ | ○ | ○ |
| Hardness in hot water | H | H | H | H | HB | HB | H | F | H |

TABLE III-4

Raw material: PET steel plate

|  | Example III | | | | | | | Comparative Example III | |
|---|---|---|---|---|---|---|---|---|---|
|  | -1 | -2 | -3 | -4 | -5 | -6 | -7 | -1 | -2 |
| Pencil hardness | 2H | 2H | H | 2H | 2H | H | 2H | HB | H |
| Impact resistance | ◉ | ○ | ◉ | ○ | ◉ | ○ | ◉ | ○ | ○ |
| Adhesion | ○ | ◉ | ○ | ○ | ◉ | ○ | ◉ | Δ | Δ |
| Hardness in hot water | HB | H | HB | H | H | H | H | F | H |
| Leveling property | ○ | ○ | ○ | ○ | ◉ | ○ | ◉ | ○ | Δ |

The ultraviolet rays-curable can-coating composition of the invention III can be cured by ultraviolet irradiation in low irradiation dose, and the resulting cured product has excellent film performances such as processability, adhesion, hardness, scratch resistance and the like, and in particular has excellent film appearance and retort resistance.

What is claimed is:

1. A liquid epoxy resin composition comprising an epoxy resin, and a curing agent and a diazabicycloundecene-based curing accelerator, wherein the epoxy resin comprises, in an amount greater than or equal to 30% by weight and less than or equal to 90% by weight of the epoxy resin, an alicyclic diepoxide compound being one of 2,2-bis(3',4'-epoxycyclohexyl)propane and di (3,4-epoxycyclohexyl)methane, together with one or more epoxy compound selected from the group consisting of 3,4-epoxycyclohexylmethyl-3',4'-epoxycyclohexane carboxylate, 3,4-epoxy-6-methylcyclohexylmethyl-3,4-epoxy-6-methylcyclohexane carboxylate, bis(3,4-epoxycyclohexyl)adipate, vinylcyclohexene monoepoxide, and limonene diepoxide.

2. The epoxy resin composition according to claim 1, wherein the alicyclic diepoxide compound is an epoxy compound produced by using percarboxylic acid having water content of 2% by weight or less.

3. The liquid epoxy resin composition according to claim 1, wherein the curing agent is an initiator which releases a substance initiating cationic polymerization by heating.

4. The liquid epoxy resin composition according to claim 1, wherein the curing agent is a liquid acid anhydride.

5. The liquid epoxy resin composition as claimed in claim 1, which is used for photosemiconductor encapsulation.

6. The liquid epoxy resin composition according to claim 1, wherein said curing accelerator is present in an amount of 0.3 to 10 parts by weight based on 100 parts by weight of the epoxy resin.

7. The liquid epoxy resin composition according to claim 1, wherein said curing accelerator is present in an amount of 1 to 10 parts by weight based on 100 parts by weight of the epoxy resin.

8. The liquid epoxy resin composition according to claim 1, wherein said curing accelerator is present in an amount of 1 to 5 parts by weight based on 100 parts by weight of the epoxy resin.

9. The liquid epoxy resin composition according to claim 1, wherein said curing accelerator is 1,8-diazabicyclo[5.4.0]undecene-7, or a salt thereof.

10. A cured product obtained by curing the liquid epoxy resin composition of claim 1.

11. The cured product according to claim 10, wherein the curing is performed by heating.

* * * * *

UNITED STATES PATENT AND TRADEMARK OFFICE
CERTIFICATE OF CORRECTION

PATENT NO. : 7,786,224 B2
APPLICATION NO. : 10/883162
DATED : August 31, 2010
INVENTOR(S) : Hideyuki Takai It is certified that error appears in the above-identified patent and that said Letters Patent is hereby corrected as shown below:

In the Specification

Column 1, line 48, please delete "has methyl group-on carbon constituting" and insert therefore -- has a methyl group on the carbon constituting the --;

Column 1, line 49, please delete "reactivity of epoxy group" and insert therefore -- reactivity of the epoxy group --;

Column 1, line 55, please delete "therefor" and insert therefore -- therefore --;

Column 1, line 60, please delete "strong acid, decrease" and insert therefore -- strong acid, a decrease --;

Column 1, line 66, please delete "the problems on" and insert therefore -- the problems of --;

Column 2, line 11, please delete "describes that a" and insert therefore -- describes a --;

Column 2, line 13, please delete "formula (I) described later is" and insert therefore -- formula (I), described later, is --;

Column 2, line 15, please delete "compound, to thereby" and insert therefore -- compound to thereby --;

Column 2, line 26, please delete "wastes" and insert therefore -- waste --;

Column 2, line 29, please delete "of such the solvent" and insert therefore -- of such a solvent --;

Column 2, line 41, please delete "moisture and heat" and insert therefore -- moisture, heat --;

Column 3, line 20, please delete "problems on hardness" and insert therefore -- problems of hardness --;

Signed and Sealed this

Thirtieth Day of November, 2010

David J. Kappos
*Director of the United States Patent and Trademark Office*

Column 3, line 31, please delete "present inventors have found" and insert therefore -- present inventor has found --;

Column 3, line 37, please delete "present inventors have found" and insert therefore -- present inventor has found --;

Column 3, line 39, please delete "and methyl group" and insert therefore -- and a methyl group --;

Column 3, line 40, please delete "on carbon" and insert therefore -- on the carbon --;

Column 3, line 47, please delete "present inventors have found" and insert therefore -- present inventor has found --;

Column 6, line 59, please delete "group which" and insert therefore -- group, which --;

Column 6, line 60, please delete "compound preferably" and insert therefore -- compound, preferably --;

Column 7, line 41, please delete "As aliphatic percarboxylic" and insert therefore -- Aliphatic percarboxylic --;

Column 7, line 63, please delete "on an apparatus or physical properties of a raw material" and insert therefore -- on the apparatus or physical properties of the raw material --;

Column 8, line 4, please delete "by reactivity" and insert therefore -- by the reactivity --;

Column 8, line 11, please delete "ated bond can" and insert therefore -- ated bonds can --;

Column 8, line 12, please delete "of unsaturated" and insert therefore -- of the unsaturated --;

Column 8, line 20, please delete "distillation, and a" and insert therefore -- distillation, or a --;

Column 8, line 26, please delete "compound" and insert therefore -- compounds --;

Column 8, line 63, please delete "method" and insert therefore -- methods --;

Column 9, line 39, please delete "affect impregnation" and insert therefore -- affect the impregnation --;

Column 9, line 45, please delete "effects as the curing" and insert therefore -- effects of a curing --;

Column 10, line 10, please delete "0.3 part by weight, curing acceleration effect is insufficient" and insert therefore -- 0.3 parts by weight, curing acceleration effects are insufficient --;

Column 11, line 66, please delete "oxetane ring in" and insert therefore -- oxetane rings in --;

Column 12, line 33, please delete "to carbon atoms" and insert therefore -- to 6 carbon atoms --;

Column 14, line 18, please delete "wherein four" and insert therefore -- wherein the four --;

Column 14, line 41, please delete "represents" and insert therefore -- represent --;

Column 14, line 66, please delete "having oxetane ring and epoxy group" and insert therefore -- having an oxetane ring and an epoxy group --;

Column 15, line 41, please delete "$R^{61}$ is ethyl" and insert therefore -- $R^{61}$ is an ethyl --;

Column 15, line 43, please delete "ethylene group, and a group" and insert therefore -- ethylene group, or a group --;

Column 15, line 58, please delete "ethyl group" and insert therefore -- ethyl groups --;

Column 16, line 20, please delete "having oxetane ring and epoxy group" and insert therefore -- having an oxetane ring and an epoxy group --;

Column 16, line 40, please delete "is ethyl group and $R^{13}$ is glycidyl group or" and insert therefore -- is an ethyl group and $R^{13}$ is a glycidyl group an --;

Column 16, line 62, please delete "containing epoxy" and insert therefore -- containing an epoxy --;

Column 17, line 1, please delete "monomer" and insert therefore -- monomers --;

Column 17, line 64, please delete "cation" and insert therefore -- cations --;

Column 18, line 6, please delete "represents aryl" and insert therefore -- represents an aryl --;

Column 20, line 62, please delete "polyol compound having" and insert therefore -- polyol compounds having --;

Column 22, line 9, please delete "particles the" and insert therefore -- particles, the --;

Column 22, line 60, please delete "dose" and insert therefore -- doses --;

Column 23, line 4, please delete "dose" and insert therefore -- doses --;

Column 23, line 8, please delete "dose" and insert therefore -- doses --;

Column 23, line 34, please delete "ray" and insert therefore -- rays --;

Column 23, line 48, please delete "like. Wavelength" and insert therefore -- like. The wavelength --;

Column 23, line 49, please delete "ray" and insert therefore -- rays --;

Column 23, line 50, please delete "Irradiation source" and insert therefore -- Irradiation sources --;

CERTIFICATE OF CORRECTION (continued)
U.S. Pat. No. 7,786,224 B2

Column 23, line 53, please delete "irradiation source of ultraviolet ray include" and insert therefore -- irradiation sources of ultraviolet rays include --;

Column 24, line 9, please delete "dose" and insert therefore -- doses --;

Column 24, line 18, please delete "for outer" and insert therefore -- for the outer --;

Column 26, line 47, please delete "300 of" and insert therefore -- 300 g of --;

Column 26, line 54, please delete "Example. Then" and insert therefore -- Example I-1. Then --;

Column 27, line 36, please delete "atm: and" and insert therefore -- atm, and --;

Column 29, line 54, please delete "in advance was" and insert therefore -- in advance, was --;

Column 31, line 44, please delete "dose becomes" and insert therefore -- doses become --;

Column 31, line 52, please delete "scratch test as" and insert therefore -- scratch tests as --;

Column 32, line 13, please delete "1 minutes, and then dipped in a 80°C" and insert therefore -- 1 minute, and then dipped in 80°C --;

Column 32, line 19, please delete "test was" and insert therefore -- tests were --;

Column 33, line 3, please delete "dose, and" and insert therefore -- doses, and --; and In claim 1, column 33, line 9, please delete "resin, and a curing" and insert therefore -- resin, a curing --.